US009308282B2

(12) United States Patent
Friebe et al.

(10) Patent No.: US 9,308,282 B2
(45) Date of Patent: Apr. 12, 2016

(54) [F-18]-LABELLED L-GLUTAMIC ACID AND L-GLUTAMINE DERIVATIVES (I), THEIR USE AND PROCESSES FOR THEIR PREPARATION

(71) Applicant: PIRAMAL IMAGING SA, Matran (CH)

(72) Inventors: Matthias Friebe, Berlin (DE); Heribert Schmitt-Willich, Berlin (DE); Matthias Berndt, Berlin (DE); Ludger Dinkelborg, Berlin (DE); Norman Koglin, Berlin (DE); Keith Graham, Berlin (DE)

(73) Assignee: PIRAMAL IMAGING SA, Matran (CH)

( * ) Notice: Subject to any disclaimer, the term of this patent is extended or adjusted under 35 U.S.C. 154(b) by 0 days.

(21) Appl. No.: 14/173,371

(22) Filed: Feb. 5, 2014

(65) Prior Publication Data

US 2014/0154183 A1 Jun. 5, 2014

Related U.S. Application Data

(63) Continuation of application No. 12/622,105, filed on Nov. 19, 2009, now abandoned, which is a continuation-in-part of application No. PCT/EP2009/003420, filed on May 14, 2009.

(30) Foreign Application Priority Data

May 20, 2008 (EP) ..................................... 08075510

(51) Int. Cl.
| | | |
|---|---|---|
| *A61K 51/00* | (2006.01) | |
| *A61M 36/14* | (2006.01) | |
| *A61K 49/04* | (2006.01) | |
| *A61K 51/04* | (2006.01) | |
| *C07B 59/00* | (2006.01) | |
| *C07C 229/24* | (2006.01) | |
| *C07C 237/06* | (2006.01) | |
| *C07C 271/22* | (2006.01) | |
| *C07D 207/28* | (2006.01) | |
| *C07C 227/16* | (2006.01) | |
| *C07C 231/12* | (2006.01) | |
| *C07C 269/06* | (2006.01) | |
| *C07C 309/66* | (2006.01) | |
| *C07D 207/16* | (2006.01) | |

(52) U.S. Cl.
CPC ......... *A61K 49/0433* (2013.01); *A61K 51/0402* (2013.01); *C07B 59/001* (2013.01); *C07C 227/16* (2013.01); *C07C 229/24* (2013.01); *C07C 231/12* (2013.01); *C07C 237/06* (2013.01); *C07C 269/06* (2013.01); *C07C 271/22* (2013.01); *C07C 309/66* (2013.01); *C07D 207/16* (2013.01); *C07D 207/28* (2013.01)

(58) Field of Classification Search
CPC ........... A61K 49/0433; A61K 51/0402; C07B 59/001; C07C 229/24; C07C 231/12; C07C 237/06; C07C 269/06; C07C 271/22; C07C 309/66; C07D 207/16
See application file for complete search history.

(56) References Cited

U.S. PATENT DOCUMENTS

| | | | |
|---|---|---|---|
| 3,444,187 | A | 5/1969 | Jisaburo et al. |
| 5,264,570 | A | 11/1993 | Johnson et al. |
| 5,589,501 | A | 12/1996 | Carrera et al. |
| 5,739,164 | A | 4/1998 | Carrera et al. |
| 7,189,383 | B2 | 3/2007 | Mertens |
| 7,483,732 | B2 | 1/2009 | Zhong et al. |
| 2002/0115688 | A1 | 8/2002 | Beart et al. |
| 2005/0240098 | A1 | 10/2005 | Zhong et al. |
| 2006/0127306 | A1 | 6/2006 | Mertens et al. |
| 2007/0081941 | A1 | 4/2007 | Mertens |
| 2010/0217011 | A1 | 8/2010 | Dinkelborg et al. |
| 2010/0290991 | A1 | 11/2010 | Friebe et al. |
| 2011/0064673 | A1 | 3/2011 | Dinkelborg et al. |
| 2011/0165076 | A1 | 7/2011 | Dinkelborg et al. |

FOREIGN PATENT DOCUMENTS

| | | |
|---|---|---|
| CA | 2667395 | 5/2008 |
| EP | 1923382 | 11/2006 |
| FR | 1461184 | 1/1966 |
| JP | 8020564 | 1/1996 |
| JP | 2006516547 | 7/2006 |
| JP | 2007532259 | 11/2007 |
| JP | 2010508317 | 3/2010 |
| WO | WO0214261 | 2/2002 |
| WO | WO0218941 | 3/2002 |
| WO | WO03099746 | 12/2003 |
| WO | WO2004110500 | 12/2004 |
| WO | WO2005101045 | 10/2005 |
| WO | WO2008052788 | 5/2008 |

OTHER PUBLICATIONS

Patel et al. Neuropharmacol. 46 (2004) 273-284.*
Baker, S. R. et al., "Radical reactions leading to substituted pyroglutamates," Tetrahedron Letters, Apr. 30, 1998, vol. 39, No. 18, pp. 2815-2818.
Baldwin, J. E. et al., "Synthesis of nonproteinogenic amino acids part 2: Preparation of a synthetic equivalent of the gamma anion synthon for asymmetric amino acid synthesis," Tetrahedron, 1989, vol. 45, No. 5, pp. 1453-1464.
Belokon, Y. N. et al., "Synthesis of enantio- and diastero-isomerically pure .beta.- and .gamma.-substituted glutamic acids via glycine condensation with activated olefins," Database CA [Online], Chemical Abstracts Service, Journal of the Chemical Society, Perkin Transactions 1: Organic and Bio-organic Chemistry, 1986, No. 11, pp. 1865-1872.
Chinese Official Action related to corresponding Chines Patent Application No. 200980118540.7 dated Oct. 29, 2013.

(Continued)

*Primary Examiner* — Michael G Hartley
*Assistant Examiner* — Sean R Donohue
(74) *Attorney, Agent, or Firm* — Millen, White, Zelano & Branigan, P.C.

(57) ABSTRACT

What is described are the compounds and the synthesis of [F-18]-labelled L-glutamic acid, [F-18]-labelled L-glutamate, their derivatives of the formula (I) and their use.

7 Claims, 5 Drawing Sheets

(56) References Cited

OTHER PUBLICATIONS

De Dios, A. et al., "4-Substituted d-Glutamic Acid Analogues: The First Potent Inhibitors of Glutamate Racemase (MurI) Enzyme with Antibacterial Activity," J. Med. Chem., 2002, vol. 45, pp. 4559-4570.
English Translation of Office Action issued Dec. 10, 2013 in related Japanese Patent Application No. 2011-509884.
English Translation of Office Action issued Dec. 10, 2013 in related Japanese Patent Application No. 2011-509883.
Escribano, A. et al., "(2S,4S)-2-Amino-4-(2,2-Diphenylethyl)Pentanedioic Acid Selective Group 2 Metabotropic Glutamate Receptor Antagonist," Bioorganic & Medicinal Chemistry Letters 8, 1998, pp. 765-770.
International Search Report for PCT/EP2007/009518 dated Jan. 28, 2008.
International Search Report for PCT/EP2009/003419 dated Aug. 24, 2009.
International Search Report for PCT/EP2009/003420 dated Aug. 26, 2009.
Jeong, M. J. et al., "Synthesis of no-carrier-added [18F]Fluoroacetate," Journal of Labelled Compounds and Radiopharmaceuticals, 1997, vol. 39, No. 5, pp. 395-399.
Laverman, P. et al., "Fluorinated amino acids for tumor imaging with positron emission tomography," European Journal of Nuclear Medicine, 2002, vol. 29, No. 5, pp. 681-690.
Office Action issued Dec. 10, 2013 in related Japanese Patent Application No. 2011-509884.
Office Action issued Dec. 10, 2013 in related Japanese Patent Application No. 2011-509883.
Office Action issued Nov. 15, 2013 in related Canadian Patent Application No. 2667395.
Pohlman, M. et al., "Efficient Stereoselective syntheses of cyclic amino acids via Michael-Induced Ring-Closing Reactions," Database Caplus [Online], Chemical Abstracts Service, Organic Letters, 2003, vol. 5, No. 15, pp. 2631-2633.
Powell, A. et al., "Precursor-directed biosynthesis of nonribosomal lipopeptides with modified glutamate residues," Chem. Commun., 2007, pp. 2683-2685.
Shiue, C. Y. et al., "Synthesis of no-carrier-added (NCA) [18F]fluoroalkyl halides and their application in the synthesis of [18F]Fluoroalkyl derivatives of neurotransmitter receptor active compounds," Journal of Labelled Compounds and Radiopharmaceuticals, 1987, vol. 24, No. 1, pp. 55-64.
Souba, W. W. et al., "Glutamine and Cancer," Annals of Surgery, 1993, vol. 218, No. 6, pp. 715-728.
Wakamiya, T. et al., "Synthesis and stereochemistry of carnosadine, a new cyclopropyl amino acid from red alga grateloupia carnosa," Tetrahedron Letters, 1986, vol. 27, No. 19, pp. 2143-2144.
Unkeless, J. C. et al., "The diastereomers of γ-Fluoroglutamate: Complementary Structural Analogues," Molecular Pharmacology, May 1971, vol. 7, pp. 293-300.
Viscontini, M. et al., "Pyrrolizidine chemistry. VII. Preparation of l-proline and trans-3-hydroxy-dl-proline by electrochemical reduction of the corresponding pyrrolidone-2-carboxylic acids," Database Caplus [Online], Chemical Abstracts Service, Helvetica Chemica Acta, 1966, vol. 49, No. 8, pp. 2524-2526.
Wu, F. et al., "Uptake of 14c- and 11c-labeled glutamate, glutamine and asparate in vitro and in vivo," Anticancer Research, Jan. 2000, vol. 20, No. 1A, pp. 251-256.
English Abstract of JP-8020564, Publication Date: Jan. 23, 1995.
English Abstract of WO03099746, Publication Date: Dec. 4, 2003.
English Abstract of EP-1923382, Publication Date: May 21, 2008.

* cited by examiner

[F-18]-LABELLED L-GLUTAMIC ACID AND L-GLUTAMINE DERIVATIVES (I), THEIR USE AND PROCESSES FOR THEIR PREPARATION

The invention relates to the subject matter referred to in the claims, i.e. [F-18]-labelled L-glutamic acid derivatives and [F-18]-labelled L-glutamine derivatives of the general formula I, and to their use and to processes for their preparation.

The early diagnosis of malignant tumour diseases plays an important role in the survival prognosis of a tumour patient. For this diagnosis, non-invasive diagnostic imaging methods are an important aid. In the last years, in particular the PET (Positron Emission Tomography) technology has been found to be particularly useful. The sensitivity and specificity of the PET technology depends essentially on the signal-giving substance (tracer) used and on its distribution in the body. In the hunt for suitable traces, one tries to make use of certain properties of tumours which differentiate tumour tissue from healthy surrounding tissue. The preferred commercial isotope used for PET applications is $^{18}F$. Owing to the short half-life of less than 2 hours, $^{18}F$ is particularly demanding when it comes to the preparation of suitable tracers. This isotope does not allow for complicated long synthesis routes and purification procedures, since otherwise a considerable amount of the radioactivity of the isotope will already have faded away before the tracer can be used for diagnosis. Accordingly, it is frequently not possible to apply established synthesis routes for non-radioactive fluorinations to the synthesis of $^{18}F$ tracers. Furthermore, the high specific activity of $^{18}F$ [about 80 GBq/nmol) leads to very low substance amounts of [$^{18}F$]-fluoride for the tracer synthesis, which in turn requires an extreme excess of precursor, making the result of a radio synthesis strategy based on a non-radioactive fluorination reaction unpredictable.

FDG ([$^{18}F$]-2-Fluorodeoxyglucose)-PET is a widely accepted and frequently used auxiliary in the diagnosis and further clinical monitoring of tumour disorders. Malignant tumours compete with the host organism for glucose as nutrient supply (Warburg O., Über den Stoffwechsel der Carcinomzelle [The metabolism of the carcinoma cell], *Biochem. Zeitschrift* 1924; 152: 309-339; Kellof G., Progress and Promise of FDG-PET Imaging for Cancer Patient Management and Oncologic Drug Development, *Clin. Cancer Res.* 2005; 11(8): 2785-2807). Compared to the surrounding cells of the normal tissue, tumour cells usually have an increased glucose metabolism. This is exploited when using fluorodeoxyglucose (FDG), a glucose derivative which is increasingly transported into the cells, where, however, it is metabolically captured as FDG 6-phosphate after phosphorylation ("Warburg effect"). Accordingly, $^{18}F$-labelled FDG is an effective tracer for detecting tumour disorders in patients using the PET technology. In the hunt for novel PET tracers, recently, amino acids have been employed increasingly for $^{18}F$ PET imaging (for example (review): *Eur. J. Nucl. Med. Mol. Imaging*. May 2002; 29(5): 681-90). Here, some of the $^{18}F$-labelled amino acids are suitable for measuring the rate of protein synthesis, but most other derivatives are suitable for measuring the direct cellular uptake in the tumour. Known $^{18}F$-labelled amino acids are derived, for example, from tyrosine amino acids, phenylalanine amino acids, proline amino acids, asparagine amino acids and unnatural amino acids (for example *J. Nucl. Med.* 1991; 32: 1338-1346, *J. Nucl. Med.* 1996; 37: 320-325, *J. Nucl. Med.* 2001; 42: 752-754 and *J. Nucl. Med.* 1999; 40: 331-338). Glutamic acid and glutamine as $^{18}F$-labelled derivatives are not known, whereas non-radioactive fluorinated glutamine and glutamic acid derivatives are known; thus, for example, those which carry fluorine in the γ-position (for example (review): *Amino Acids* April 2003; 24(3): 245-61) or in the β-position (for example *Tetrahedron Lett.* 1989; 30(14): 1799-1802, *J. Org. Chem.* 1989; 54(2): 498-500, Tetrahedron: Asymmetry 2001; 12(9): 1303-1312).

Glutamic acid derivatives having protective groups at the chemical functionalities and a leaving group in the β- or γ-position have already been reported in the past. Thus, there has been a report of glutamate having mesylate or bromide in the γ-position whose acid and amine functions were provided with ester and Z protective groups, respectively, (*J. Chem. Soc. Perkin Trans.* 1; 1986; 1323-1328) or, for example, of γ-chloroglutamic acid without protective groups (*Synthesis*; (1973); 44-46). There have also been various reports of similar derivatives where the leaving group was located in the β-position: for example *Chem. Pharm. Bull.*; 17; 5; (1969); 879-885, *J. Gen. Chem. USSR* (Engl. Transl.); 38; (1968); 1645-1648; *Tetrahedron Lett.*, 27; 19; (1986); 2143-2144, *Chem. Pharm. Bull.*; EN; 17; 5; 1969; 873-878, Patent FR 1461184, Patent JP 13142.

The PET tracers currently used in tumour diagnosis have some undisputed disadvantages: thus, FDG is preferably accumulated in cells having an elevated glucose metabolism; however, under different pathological and physiological conditions, as also in elevated glucose metabolism in the cells and tissues involved, for example infection sites or wound healing (summarized in *J. Nucl. Med. Technol.* (2005), 33, 145-155). Frequently, it is still difficult to ascertain whether a lesion detected via FDG-PET is really of neoplastic origin or is the result of other physiological or pathological conditions of the tissue. Overall, the diagnosis by FDG-PET in oncology has a sensitivity of 84% and a specificity of 88% (Gambhir et al., "A tabulated summary of the FDG PET literature", *J. Nucl. Med.* 2001, 42, 1-93S). The imaging of brain tumours, for example, is very difficult owing to the high accumulation of FDG in healthy brain tissue.

In some cases, the $^{18}F$-labelled amino acid derivatives currently known are well suited for the detection of tumours in the brain ((review): *Eur. J. Nucl. Med. Mol. Imaging.* 2002 May; 29(5): 681-90); however, in the case of other tumours, they are not able to compete with the imaging properties of the "Goldstandard" [$^{18}F$]2-FDG. The metabolic accumulation and retention of the current F-18-labelled amino acids in tumour tissue is generally lower than of FDG. In addition, the preparation of isomerically pure F-18-labelled non-aromatic amino acids is chemically very demanding.

Similarly to glucose, for glutamic acid and glutamine, too, an increased metabolism in proliferating tumour cells has been described (Medina, *J. Nutr.* 1131: 2539S-2542S, 2001; Souba, Ann Surg 218: 715-728, 1993). The increased rate of protein and nucleic acid syntheses and the energy generation per se are thought to be the reasons for an increased glutamine consumption of tumour cells. The synthesis of corresponding C-11- and C-14-labelled compounds, which are thus identical to the natural substrate, has already been described in the literature (for example Antoni, Enzyme Catalyzed Synthesis of L-[4-C-11]aspartate and L-[5-C-11]glutamate. *J. Labelled Compd. Radiopharm.* 44; (4) 2001: 287-294 and Buchanan, The biosynthesis of showdomycin: studies with stable isotopes and the determination of principal precursors, *J. Chem. Soc. Chem. Commun.*; EN; 22; 1984; 1515-1517). First tests with the C-11-labelled compound indicate no significant accumulation in tumours.

It is an object of the present invention to provide novel compounds which, in [$^{18}F$]-labelled form, are suitable for PET-based diagnosis.

This object is achieved by the provision according to the invention of [$^{18}$F]-labelled glutamic acid derivatives and [$^{18}$F]-labelled glutamine derivatives of the general formula (I), including diastereomers:

$$\text{A}-\overset{\text{O}}{\underset{\overset{\vdots}{R^1}}{\text{C}}}-\overset{R^2}{\underset{}{\text{CH}}}-\overset{}{\underset{NH_2}{\text{CH}}}-\overset{\text{O}}{\underset{}{\text{C}}}-\text{G} \qquad (I)$$

in which
A represents
a) hydroxyl,
b) branched or straight-chain $C_1$-$C_5$ alkoxy,
c) branched or straight-chain hydroxy $C_1$-$C_5$ alkoxy,
d) branched or straight-chain O—$C_1$-$C_5$ alkyl-(O—$C_1$-$C_4$ alkyl), —O—$C_1$-$C_4$ alkyl,
e) N($C_1$-$C_5$ alkyl)$_2$,
f) NH$_2$,
g) N(H)-L,
h) O-L or
i) O—Z,
G represents
a) hydroxyl,
b) O—Z,
c) branched or straight-chain O—$C_1$-$C_5$ alkyl,
d) branched or straight-chain O—$C_2$-$C_5$ alkenyl,
e) branched or straight-chain O—$C_1$-$C_5$ alkyl-(O—$C_1$-$C_4$ alkyl), —O—$C_1$-$C_4$ alkyl,
f) branched or straight-chain O—$C_2$-$C_5$ alkynyl or
g) triphenylmethoxy,
$R^1$ and $R^2$ represent
a) hydrogen,
b) branched or straight-chain $^{18}$F—$C_1$-$C_5$ alkoxy,
c) branched or straight-chain $^{18}$F—$C_1$-$C_5$ alkyl,
d) branched or straight-chain $^{18}$F—$C_2$-$C_5$ alkenyl,
e) branched or straight-chain $^{18}$F—$C_2$-$C_5$ alkynyl,
f) hydroxyl,
g) branched or straight-chain $C_1$-$C_5$ alkyl or
h) branched or straight-chain $C_1$-$C_5$ alkoxy, alkyl being optionally interrupted by one or more O, S or N,
with the proviso that one of the substituents $R^1$ or $R^2$ contains exactly one $^{18}$F isotope and the respective other substituent contains no $^{18}$F isotope, with the proviso that $R^1$ is not hydrogen,
L represents
a) branched or straight-chain $C_1$-$C_5$ alkyl,
b) branched or straight-chain $C_2$-$C_5$ alkenyl,
c) branched or straight-chain $C_1$-$C_5$ alkyl-(O—$C_1$-$C_4$ alkyl)$_n$-O—$C_1$-$C_4$ alkyl or
d) branched or straight-chain $C_2$-$C_5$ alkynyl,
Z represents a metal cation equivalent, and
where n=0, 1, 2 or 3.
Preferred compounds according to the invention of the formula (I) are distinguished in that
A represents
a) hydroxyl,
b) methoxy,
c) ethoxy,
d) propoxy,
e) NMe$_2$,
f) NEt$_2$,
g) NH$_2$,
h) N(H)-L,
i) O-L or
j) O—Z.
Further preferred compounds according to the invention of the formula (I) are distinguished in that
A represents
a) hydroxyl,
b) methoxy,
c) ethoxy,
d) NMe$_2$,
e) NH$_2$ or
f) N(H)-L.
Particularly preferred compounds according to the invention of the formula (I) are distinguished in that
A represents
a) hydroxyl,
b) branched or straight-chain $C_1$-$C_5$ alkoxy or
c) NH$_2$.
Preferred compounds according to the invention of the formula (I) are distinguished in that
A represents
hydroxyl.
Preferred compounds according to the invention of the formula (I) are distinguished in that
A represents
NH$_2$.
Preferred compounds according to the invention of the formula (I) are distinguished in that
A represents
ethoxy.
Preferred compounds according to the invention of the formula (I) are distinguished in that
G represents
a) hydroxyl,
b) branched or straight-chain O—$C_1$-$C_4$ alkyl or
c) O—$C_2$H$_4$—OMe.
Further preferred compounds according to the invention of the formula (I) are distinguished in that
G represents
a) hydroxyl or
b) branched or straight-chain O—$C_1$-$C_4$ alkyl.
Particularly preferred compounds according to the invention of the formula (I) are distinguished in that
G represents
a) hydroxyl,
or
b) ethoxy.
Particularly preferred compounds according to the invention of the formula (I) are distinguished in that
G represents
hydroxyl.
Preferred compounds according to the invention of the formula (I) are distinguished in that
$R^1$ and $R^2$ represent
a) hydrogen,
b) branched or straight-chain $^{18}$F—$C_1$-$C_5$ alkoxy,
c) branched or straight-chain $^{18}$F—$C_1$-$C_5$ alkyl,
d) branched or straight-chain $^{18}$F—$C_3$-$C_5$ alkenyl,
e) branched or straight-chain $^{18}$F—$C_3$-$C_5$ alkynyl,
f) hydroxyl,
g) branched or straight-chain $C_1$-$C_5$ alkyl or
h) branched or straight-chain $C_1$-$C_5$ alkoxy.
Preferred compounds according to the invention of the formula (I) are distinguished in that
$R^1$ and $R^2$ represent
a) hydrogen,
b) branched or straight-chain $^{18}$F—$C_2$-$C_4$ alkoxy, c) branched or straight-chain $^{18}F$—$C_3$-$C_5$ alkyl,
d) branched or straight-chain $^{18}F$—$C_3$-$C_5$ alkenyl,
e) branched or straight-chain $^{18}F$—$C_3$-$C_5$ alkynyl,
f) hydroxyl,
g) branched or straight-chain $C_1$-$C_5$ alkyl or
h) branched or straight-chain $C_1$-$C_5$ alkoxy,
with the proviso that one of the substituents $R^1$ or $R^2$ contains exactly one $^{18}F$-isotope and the respective other substituent contains no $^{18}F$ isotope, with the proviso that $R^1$ is not hydrogen.

A further particular subject matter of the invention are compounds of the general formula I in which
$R^1$ represents
a) branched or straight-chain $^{18}F$—$C_2$ alkoxy,
b) branched or straight-chain $^{18}F$—$C_3$ alkyl.
Straight-chain $^{18}F$—$C_2$ alkoxy is $^{18}F$-ethoxy.
Straight-chain $^{18}F$—$C_3$ alkyl is $^{18}F$-propyl.

A further particular subject matter of the invention are compounds of the general formula I in which
$R^1$ represents $^{18}F$-ethoxy or $^{18}F$-propyl and $R^2$ represents hydrogen.

Further preferred compounds according to the invention of the formula (I) are distinguished in that
$R^1$ is selected from the group consisting of $^{18}F$-ethoxy, $^{18}F$-propoxy, $^{18}F$-ethyl and $^{18}F$-propyl, and $R^2$ is hydrogen.

Preferred compounds according to the invention of the formula (I) are distinguished in that
L represents
a) methyl,
b) ethyl,
c) propyl,
d) isopropyl,
e) —$C_2H_4$—OMe or
f) —$C_2H_4$—O—$O_2H_4$—OMe.

Particularly preferred compounds according to the invention of the formula (I) are distinguished in that
L represents
a) methyl or
b) ethyl.

Compounds according to the invention of the formula (I) which are likewise preferred are distinguished in that Z is selected from the group consisting of $Na^+$, $K^+$, $Ca^{2+}$ and $Mg^{2+}$. Z is preferably $Na^+$.

The process for preparing the compounds according to the invention of the general formula (I) is distinguished in that
one or more protective groups present in a compound of the formula (II) is/are removed.

Compounds according to formula I:

a)

b)

c)

d)

e) and f)

At physiological pH 7.4, the compounds of the formula (I) according to the invention may also be present as zwitterions or salts, as is known to those skilled in the art.

According to a further aspect, the present invention thus relates to compounds of the general formula (II):

(II)

A' represents
a) hydroxyl,
b) branched or straight-chain $C_1$-$C_5$ alkoxy,
c) branched or straight-chain hydroxy $C_1$-$C_5$ alkoxy,
d) branched or straight-chain O—$C_1$-$C_5$ alkyl-(O—$C_1$-$C_4$ alkyl), —O—$C_1$-$C_4$ alkyl,
e) N($C_1$-$C_5$ alkyl)$_2$,
f) $NH_2$,
g) N(H)-L', or
h) O-L',
G' represents
a) hydroxyl,
b) O—Z,
c) branched or straight-chain O—$C_1$-$C_5$ alkyl,
d) branched or straight-chain O—$C_2$-$C_5$ alkenyl,
e) branched or straight-chain O—$C_1$-$C_5$ alkyl-(O—$C_1$-$C_4$ alkyl), —O—$C_1$-$C_4$ alkyl,
f) branched or straight-chain O—$C_2$-$C_5$ alkynyl or
g) triphenylmethoxy,
$R^1$ and $R^2$ represent
a) hydrogen,
b) branched or straight-chain $^{18}F$—$C_1$-$C_5$ alkoxy,
c) branched or straight-chain $^{18}F$—$C_1$-$C_5$ alkyl,
d) branched or straight-chain $^{18}F$—$C_2$-$C_5$ alkenyl,
e) branched or straight-chain $^{18}F$—$C_2$-$C_5$ alkynyl,
f) hydroxyl,
g) branched or straight-chain $C_1$-$C_5$ alkyl or
h) branched or straight-chain $C_1$-$C_5$ alkoxy,
alkyl being optionally interrupted by one or more O, S or N, with the proviso that exactly one of the substituents $R^1$ or $R^2$ contains exactly one $^{18}F$ isotope and the respective other substituent contains no $^{18}F$ isotope, with the proviso that $R^1$ is not hydrogen,
Q represents
a) N(H)-tert-butoxycarbonyl
b) N(H)-allyloxycarbonyl,
c) N(H)-benzyloxycarbonyl,
d) N(H)-ethoxycarbonyl,
e) N(H)-methoxycarbonyl,
f) N(H)-propoxycarbonyl,
e) N(H)-2,2,2-trichloroethoxycarbonyl,
f) N(H)-1,1-dimethylpropynyl,
g) N(H)-1-methyl-1-phenylethoxycarbonyl,
h) N(H)-1-methyl-1-(4-biphenylyl)ethoxycarbonyl,
i) N(H)-cyclobutylcarbonyl,
j) N(H)-1-methylcyclobutylcarbonyl,
k) N(H)-vinylcarbonyl,
l) N(H)-allylcarbonyl,
m) N(H)-adamantylcarbonyl,
n) N(H)-diphenylmethylcarbonyl,
o) N(H)-cinnamylcarbonyl,
p) N(H)-formyl,
q) N(H)-benzoyl,
r) N(H)-trityl,
s) N(H)-p-methoxydiphenylmethyl,
t) N(H)-di(p-methoxyphenyl)phenylmethyl, u) 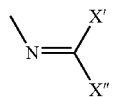

or
v) N-(tert-butoxycarbonyl)$_2$,
L' represents
a) branched or straight-chain $C_1$-$C_5$ alkyl,
b) branched or straight-chain $C_2$-$C_5$ alkenyl,
c) branched or straight-chain $C_1$-$C_5$ alkyl-(O—$C_1$-$C_4$ alkyl), —O—$C_1$-$C_4$ alkyl or
d) branched or straight-chain $C_2$-$C_5$ alkynyl,
X' and X" independently of one another represent
a) branched or straight-chain $C_1$-$C_5$ alkyl,
b) substituted or unsubstituted aryl,
c) substituted or unsubstituted aralkyl or
d) substituted or unsubstituted heteroaryl,
Z' represents a metal cation equivalent, and
where n=0, 1, 2 or 3.
Preferred compounds according to the invention of the formula (II) are distinguished in that
A' represents
a) hydroxyl,
b) methoxy,
c) ethoxy,
d) propoxy,
e) $NMe_2$,
f) $NEt_2$,
g) $NH_2$,
h) N(H)-L or
i) O-L,
j) O—Z.
Further preferred compounds according to the invention of the formula (II) are distinguished in that
A' represents
a) hydroxyl,
b) methoxy,
c) ethoxy,
d) $NMe_2$,
e) $NH_2$ or
f) N(H)-L.
Particularly preferred compounds according to the invention of the formula (II) are distinguished in that
A' represents
a) hydroxyl,
b) branched or straight-chain $C_1$-$C_5$ alkoxy or
c) $NH_2$.
Preferred compounds according to the invention of the formula (II) are distinguished in that
A' represents
tert-butoxy.
Preferred compounds according to the invention of the formula (II) are distinguished in that A' represents $NH_2$.
Preferred compounds according to the invention of the formula (II) are distinguished in that
A' represents
ethoxy.
Preferred compounds according to the invention of the formula (II) are distinguished in that
G' represents
a) hydroxyl,
b) branched or straight-chain O—$C_1$-$C_4$ alkyl or
c) O—$C_2H_4$—OMe.
Further preferred compounds according to the invention of the formula (II) are distinguished in that
G' represents
a) hydroxyl or
b) branched or straight-chain O—$C_1$-$C_4$ alkyl.
Particularly preferred compounds according to the invention of the formula (II) are distinguished in that
G' represents
a) hydroxyl,
b) methoxy, c) ethoxy or
d) tert-butoxy.

Particularly preferred compounds according to the invention of the formula (II) are distinguished in that
G' represents
tert-butoxy.

Preferred compounds according to the invention of the formula (II) are distinguished in that
$R^1$ and $R^2$ represent
a) hydrogen,
b) branched or straight-chain $^{18}F$—$C_1$-$C_5$ alkoxy,
c) branched or straight-chain $^{18}F$—$C_1$-$C_5$ alkyl,
d) branched or straight-chain $^{18}F$—$C_3$-$C_5$ alkenyl,
e) branched or straight-chain $^{18}F$—$C_3$-$C_5$ alkynyl,
f) hydroxyl,
g) branched or straight-chain $C_1$-$C_5$ alkyl or
h) branched or straight-chain $C_1$-$C_5$ alkoxy,
with the proviso that exactly one of the substituents $R^1$ or $R^2$ contains exactly one $^{18}F$-isotope and the respective other substituent contains no $^{18}F$ isotope, with the proviso that $R^1$ is not hydrogen.

Preferred compounds according to the invention of the formula (II) are distinguished in that
$R^1$ and $R^2$ represent
a) hydrogen,
b) branched or straight-chain $^{18}F$—$C_2$-$C_4$ alkoxy,
c) branched or straight-chain $^{18}F$—$C_3$-$C_5$ alkyl,
d) branched or straight-chain $^{18}F$—$C_3$-$C_5$ alkenyl,
e) branched or straight-chain $^{18}F$—$C_3$-$C_5$ alkynyl,
f) hydroxyl,
g) branched or straight-chain $C_1$-$C_5$ alkyl or
h) branched or straight-chain $C_1$-$C_5$ alkoxy,
with the proviso that exactly one of the substituents $R^1$ or $R^2$ contains exactly one $^{18}F$-isotope and the respective other substituent is hydrogen, with the proviso that $R^1$ is not hydrogen.

Preferred compounds according to the invention of the formula (II) are distinguished in that $R^1$ is selected from the group consisting of $^{18}F$-ethoxy, $^{18}F$-propoxy, $^{18}F$-ethyl and $^{18}F$-propyl, and $R^2$ is hydrogen.

A further particular subject matter of the invention are compounds of the general formula II in which
$R^1$ represents
a) branched or straight-chain $^{18}F$—$C_2$ alkoxy or
b) branched or straight-chain $^{18}F$—$C_3$ alkyl.
Straight-chain $^{18}F$—$C_2$ alkoxy is $^{18}F$-ethoxy.
Straight-chain $^{18}F$—$C_3$ alkyl is $^{18}F$-propyl.

A further particular subject matter of the invention are compounds of the general formula II in which
$R^1$ represents $^{18}F$-ethoxy or $^{18}F$-propyl and $R^2$ represents hydrogen.

Preferred compounds according to the invention of the formula (II) are distinguished in that
L' represents
a) methyl,
b) ethyl,
c) propyl,
d) isopropyl,
e) —$C_2H_4$-OMe,
f) —$C_2H_4$—O—$O_2H_4$—$OCH_3$ or
g) tert-butyl.

Particularly preferred compounds according to the invention of the formula (II) are distinguished in that
L' represents
a) methyl,
b) ethyl or
c) tert-butyl.

Compounds according to the invention of the formula (II) which are likewise preferred are distinguished in that Z is selected from the group consisting of $Na^+$, $K^+$, $Ca^{2+}$ and $Mg^{2+}$. Z' is preferably $Na^+$.

Preferred compounds according to the invention of the formula (II) are distinguished in that
Q represents
a) N(H)-tert-butoxycarbonyl,
b) N(H)-benzyloxycarbonyl,
c) N-(tert-butoxycarbonyl)$_2$ or d)

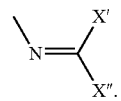

Further preferred compounds according to the invention of the formula (II) are distinguished in that
Q represents
a) N(H)-tert-butoxycarbonyl,
b) N-(tert-butoxycarbonyl)$_2$ or c)

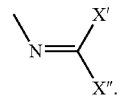

Particularly preferred compounds according to the invention of the formula (II) are distinguished in that
Q represents
a) N(H)-tert-butoxycarbonyl or b)

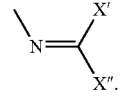

Particularly preferred compounds according to the invention of the formula (II) are distinguished in that
Q represents N(H)-tert-butoxycarbonyl.

Preferred compounds according to the invention of the formula (II) are distinguished in that
X' and X" independently of one another represent
a) branched or straight-chain $C_1$-$C_5$ alkyl,
b) substituted or unsubstituted aryl or
c) substituted or unsubstituted aralkyl.

Further preferred compounds according to the invention of the formula (II) are distinguished in that
X' and X" independently of one another represent
a) branched or straight-chain $C_1$-$C_5$ alkyl or
b) substituted or unsubstituted aryl.

Particularly preferred compounds according to the invention of the formula (II) are distinguished in that
X' and X" represent phenyl or represent phenyl which is substituted in the 2-position.

The process for preparing the compounds of the general formula (II) according to the invention is distinguished in that the plurality of the compound according to formula (II) can be formed from a compound of the formula (III) following introduction of the $^{18}F$-isotope.

Process for preparing compounds of the general formula (II) which comprises
reacting a compound of the formula (III) with F-18 fluoride.

Compounds of the formula I, II or III for use as medicament.

Compounds of the formula I, II or III for use for imaging of tumour disorders.

Use of compounds of the formula I, II or III for preparing a medicament for imaging of tumour disorders.

According to a further aspect, the present invention relates to compounds of the general formula (III):

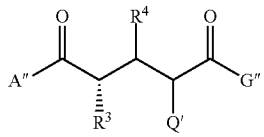

(III)

in which
A'' represents
a) branched or straight-chain $C_1$-$C_5$ alkoxy,
b) branched or straight-chain hydroxy $C_1$-$C_5$ alkoxy,
c) branched or straight-chain O—$C_1$-$C_5$ alkyl-(O—$C_1$-$C_4$ alkyl), —O—$C_1$-$C_4$ alkyl,
d) N($C_1$-$C_5$ alkyl)$_2$,
e) NH$_2$,
f) N(H)-L'', or
g) O-L'',
G'' represents
a) O—Z'',
b) branched or straight-chain O—$C_1$-$C_5$ alkyl,
c) branched or straight-chain O—$C_2$-$C_5$ alkenyl,
d) branched or straight-chain O—$C_1$-$C_5$ alkyl-(O—$C_1$-$C_4$ alkyl), —O—$C_1$-$C_4$ alkyl,
e) branched or straight-chain O—$C_2$-$C_5$ alkynyl or
f) triphenylmethoxy,
$R^3$ and $R^4$ represent
a) hydrogen,
b) branched or straight-chain E-$C_1$-$C_5$ alkoxy,
c) branched or straight-chain E-$C_1$-$C_5$ alkyl,
d) branched or straight-chain E-$C_2$-$C_5$ alkenyl,
e) branched or straight-chain E-$C_2$-$C_5$ alkynyl,
f) hydroxyl,
g) branched or straight-chain $C_1$-$C_5$ alkyl or
h) branched or straight-chain $C_1$-$C_5$ alkoxy,
alkyl being optionally interrupted by one or more O, S or N,
with the proviso that exactly one of the substituents $R^3$ or $R^4$ contains an E and the respective other substituent contains no E, with the proviso that $R^3$ is not hydrogen,
E represents a leaving group,
Q' represents
a) N(H)-tert-butoxycarbonyl
b) N(H)-allyloxycarbonyl,
c) N(H)-benzyloxycarbonyl,
d) N(H)-ethoxycarbonyl,
e) N(H)-methoxycarbonyl,
f) N(H)-propoxycarbonyl,
g) N(H)-2,2,2-trichloroethoxycarbonyl,
h) N(H)-1,1-dimethylpropynyl,
i) N(H)-1-methyl-1-phenylethoxycarbonyl,
j) N(H)-1-methyl-1-(4-biphenylyl)ethoxycarbonyl,
k) N(H)-cyclobutylcarbonyl,
l) N(H)-1-methylcyclobutylcarbonyl,
m) N(H)-vinylcarbonyl,
n) N(H)-allylcarbonyl,
o) N(H)-adamantylcarbonyl,
p) N(H)-diphenylmethylcarbonyl,
q) N(H)-cinnamylcarbonyl,
r) N(H)-formyl,
s) N(H)-benzoyl,
t) N(H)-trityl,
u) N(H)-p-methoxyphenyldiphenylmethyl,
v) N(H)-di(p-methoxyphenyl)phenylmethyl, w)

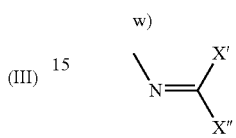

or
x) N-(tert-butoxycarbonyl)$_2$,
L'' represents
a) branched or straight-chain $C_1$-$C_5$ alkyl,
b) branched or straight-chain $C_2$-$C_5$ alkenyl,
c) branched or straight-chain $C_1$-$C_5$ alkyl-(O—$C_1$-$C_4$ alkyl), —O—$C_1$-$C_4$ alkyl or
d) branched or straight-chain $C_2$-$C_5$ alkynyl,
X' and X'' independently of one another represent
a) branched or straight-chain $C_1$-$C_5$ alkyl,
b) substituted or unsubstituted aryl,
c) substituted or unsubstituted alkylaryl or
d) substituted or unsubstituted heteroaryl,
Z'' represents a metal cation equivalent, and
where n=0, 1, 2 or 3.

Preferred compounds according to the invention of the general formula (III) are distinguished in that
A'' represents
a) branched or straight-chain $C_1$-$C_5$ alkoxy or
b) NH$_2$.

Further preferred compounds according to the invention of the general formula (III) are distinguished in that
A'' represents
a) methoxy,
b) ethoxy,
c) NH$_2$ or
d) tert-butoxy.

Preferred compounds according to the invention of the general formula (III) are distinguished in that
A'' represents
methoxy.

Preferred compounds according to the invention of the general formula (III) are distinguished in that
A'' represents
NH$_2$.

Preferred compounds according to the invention of the general formula (III) are distinguished in that
A'' represents
ethoxy.

Preferred compounds according to the invention of the general formula (III) are distinguished in that
A'' represents
tert-butoxy.

Preferred compounds according to the invention of the general formula (III) are distinguished in that
G'' represents
a) branched or straight-chain O—$C_1$-$C_5$ alkyl,
b) branched or straight-chain O—$C_2$-$C_5$ alkenyl, c) branched or straight-chain O—$C_1$-$C_5$ alkyl-(O—$C_1$-$C_4$ alkyl), —O—$C_1$-$C_4$ alkyl or
e) triphenylmethoxy.

Further preferred compounds according to the invention of the general formula (III) are distinguished in that
G" represents
a) methoxy,
b) ethoxy, or
c) tert-butoxy.

Particularly preferred compounds according to the invention of the general formula (III) are distinguished in that
G" represents
a) tert-butoxy.

Preferred compounds according to the invention of the general formula (III) are distinguished in that
$R^3$ and $R^4$ represent
a) hydrogen,
b) branched or straight-chain E-$C_1$-$C_5$ alkoxy,
c) branched or straight-chain E-$C_1$-$C_5$ alkyl,
d) branched or straight-chain E-$C_3$-$C_5$ alkenyl,
e) branched or straight-chain E-$C_3$-$C_5$ alkynyl,
f) hydroxyl,
g) branched or straight-chain $C_1$-$C_5$ alkyl or
h) branched or straight-chain $C_1$-$C_5$ alkoxy,
with the proviso that exactly one of the substituents $R^3$ or $R^4$ contains an E and the respective other substituent contains no E, with the proviso that $R^3$ is not hydrogen.

Preferred compounds according to the invention of the general formula (III) are distinguished in that
$R^3$ and $R^4$ represent
a) hydrogen,
b) branched or straight-chain E-$C_2$-$C_4$ alkoxy,
c) branched or straight-chain E-$C_3$-$C_5$ alkyl,
d) branched or straight-chain E-$C_3$-$C_5$ alkenyl,
e) branched or straight-chain E-$C_3$-$C_5$ alkynyl,
f) branched or straight-chain $C_1$-$C_5$ alkyl or
g) branched or straight-chain $C_1$-$C_5$ alkoxy,
with the proviso that exactly one of the substituents $R^3$ or $R^4$ contains an E and the respective other substituent is hydrogen, with the proviso that $R^3$ is not hydrogen.

Preferred compounds according to the invention of the general formula (III) are distinguished in that
$R^3$ and $R^4$ represent
a) hydrogen,
b) branched or straight-chain E-$C_2$ alkoxy,
c) branched or straight-chain E-$C_3$ alkyl,
d) branched or straight-chain E-$C_3$ alkenyl or
e) branched or straight-chain E-$C_3$ alkynyl,
f) hydroxyl,
g) branched or straight-chain $C_1$-$C_5$ alkyl or
h) branched or straight-chain $C_1$-$C_5$ alkoxy,
with the proviso that exactly one of the substituents $R^3$ or $R^4$ contains an E and the respective other substituent does not contain an E.

A further particular subject matter of the invention are compounds of the general formula III in which
$R^3$ represents
a) branched or straight-chain E-$C_2$ alkoxy or
b) branched or straight-chain E-$C_3$ alkyl.

Straight-chain E-$C_2$ alkoxy is E-ethoxy.
Straight-chain E-$C_3$ alkyl is E-propyl.

A further particular subject matter of the invention are compounds of the general formula (III) in which
$R^3$ represents E-ethoxy or E-propyl and $R^4$ represents hydrogen.

E is a leaving group which is known or obvious to the person skilled in the art and which is described or mentioned, for example, in Synthese (1982), pages 85-125, Table 2, page 86; Carey and Sundberg, Organische Synthese, (1995), pages 279-281, Table 5.8; or Netscher, Recent Res. Dev. Org. Chem., 2003, 7, 71-83, schemes 1, 2, 10 and 15 or in Jerry March, Advanced Organic Chemistry, 4th edition, John Wiley and Sons, pp. 351-56 and 642-653), without being limited thereto.

Preferred compounds according to the invention of the general formula (III) are distinguished in that
E represents
halogen or
sulphonyloxy.

Preferred halogens are iodo, bromo and chloro.
Preferred sulphonyloxy are methanesulphonyloxy, trifluoromethanesulphonyloxy, nonafluorobutyloxy, tosyloxy and nosyloxy.

Preferred compounds according to the invention of the general formula (III) are distinguished in that
E represents
a) chloro,
b) bromo,
c) methanesulphonyloxy,
d) trifluoromethanesulphonyloxy,
e) nonafluorobutyloxy,
f) tosyloxy or
g) iodo.

Preferred compounds according to the invention of the general formula (III) are distinguished in that
E represents
a) chloro,
b) bromo,
c) methanesulphonyloxy,
d) trifluoromethanesulphonyloxy,
e) tosyloxy or
f) iodo.

Further preferred compounds according to the invention of the general formula (III) are distinguished in that
E represents
a) bromo,
b) methanesulphonyloxy,
d) trifluoromethanesulphonyloxy.

Particularly preferred compounds according to the invention of the general formula (III) are distinguished in that
E represents
a) bromo, or
b) methanesulphonyloxy.

Preferred compounds according to the invention of the general formula (III) are distinguished in that
Q' represents
a) N(H)-tert-butoxycarbonyl,
b) N(H)-benzyloxycarbonyl,
c) N(H)-trityl or d)

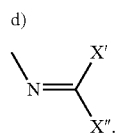

Further preferred compounds according to the invention of the general formula (III) are distinguished in that
Q' represents
a) N(H)-tert-butoxycarbonyl or b)
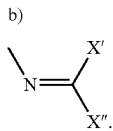

Preferred compounds according to the invention of the formula (III) are distinguished in that L" represents
a) branched or straight-chain $C_1$-$C_5$ alkyl,
b) branched or straight-chain $C_2$-$C_5$ alkenyl or
c) branched or straight-chain $C_2$-$C_5$ alkynyl.

Preferred compounds according to the invention of the formula (III) are distinguished in that
L" represents
a) methyl,
b) ethyl,
c) propyl,
d) isopropyl,
e) —$C_2H_4$—OMe or
f) —$C_2H_4$—O—$C_2H_4$—OMe.

Further preferred compounds according to the invention of the formula (III) are distinguished in that
L" represents
a) methyl, or
b) ethyl.

Preferred compounds according to the invention of the formula (III) are distinguished in that
X' and X" independently of one another represent
a) branched or straight-chain $C_1$-$C_5$ alkyl,
b) substituted or unsubstituted aryl or
c) aralkyl.

Further preferred compounds according to the invention of the formula (III) are distinguished in that
X' and X" independently of one another represent
a) branched or straight-chain $C_1$-$C_5$ alkyl or
b) substituted or unsubstituted aryl.

Particularly preferred compounds according to the invention of the formula (III) are distinguished in that
X' and X" represent phenyl or phenyl which is substituted in the 2-position.

Compounds according to the invention of the formula (III) which are likewise preferred are distinguished in that Z' is selected from the group consisting of $NA^+$, $K_+$, $Ca^{2+}$ and $Mg^{2+}$. Z' is preferably $Na^+$.

According to a further aspect, the present invention thus relates to the use of compounds of the formula (IV) for preparing compounds of the formula (I) or (II):

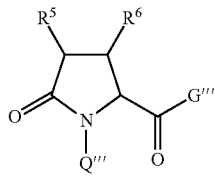
(IV)

in which
G''' represents
a) branched or straight-chain O—$C_1$-$C_5$ alkyl,
b) branched or straight-chain O—$C_2$-$C_5$ alkenyl,
c) branched or straight-chain O—$C_1$-$C_5$ alkyl-(O—$C_1$-$C_4$ alkyl), —O—$C_1$-$C_4$ alkyl,
d) branched or straight-chain O—$C_2$-$C_5$ alkynyl or
e) triphenylmethoxy,
$R^5$ and $R^6$ represent
a) hydrogen,
b) hydroxyl,
c) branched or straight-chain $C_1$-$C_5$ alkyl,
d) branched or straight-chain $C_1$-$C_5$ alkoxy or
e) $R^7$-E',
alkyl being optionally interrupted by one or more O, S or N, with the proviso that exactly one of the substituents $R^5$ or $R^6$ contains an E' and the respective other substituent contains no E', with the proviso that $R^5$ is not hydrogen,
E' represents a leaving group,
$R^7$ represents
a) branched or straight-chain $C_1$-$C_5$ alkoxy,
b) branched or straight-chain $C_1$-$C_5$ alkyl,
c) branched or straight-chain $C_2$-$C_5$ alkenyl or
d) branched or straight-chain $C_2$-$C_5$ alkynyl,
Q''' represents
a) N-tert-butoxycarbonyl
b) N-allyloxycarbonyl,
c) N-benzyloxycarbonyl,
d) N-ethoxycarbonyl,
e) N-methoxycarbonyl,
f) N-propoxycarbonyl,
g) N-2,2,2-trichloroethoxycarbonyl,
h) hydrogen,
i) N-1-methyl-1-phenylethoxycarbonyl,
j) N-1-methyl-1-(4-biphenylyl)ethoxycarbonyl,
k) N-cyclobutylcarbonyl,
l) N-1-methylcyclobutylcarbonyl,
m) N-vinylcarbonyl,
n) N-allylcarbonyl,
o) N-adamantylcarbonyl,
p) N-diphenylmethylcarbonyl,
q) N-cinnamylcarbonyl,
r) N-formyl,
s) N-benzoyl,
t) N(H)-trityl,
u) N(H)-p-methoxyphenyldiphenylmethyl,
v) N(H)-di(p-methoxyphenyl)phenylmethyl, w)
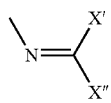

or
x) N-(tert-butoxycarbonyl)$_2$,
X' and X" independently of one another represent
a) branched or straight-chain $C_1$-$C_5$ alkyl,
b) substituted or unsubstituted aryl,
c) substituted or unsubstituted alkylaryl or
d) substituted or unsubstituted heteroaryl, and
where n=0, 1, 2 or 3.

Particularly preferred compounds according to the invention of the formula (IV) are distinguished in that
G''' represents
a) branched or straight-chain O—$C_1$-$C_5$ alkyl,
b) branched or straight-chain O—$C_2$-$C_5$ alkenyl, c) branched or straight-chain O—$C_1$-$C_5$ alkyl-(O—$C_1$-$C_4$ alkyl), —O—$C_1$-$C_4$ alkyl or
e) triphenylmethoxy.

Further preferred compounds according to the invention of the formula (IV) are distinguished in that
G''' represents
a) methoxy,
b) ethoxy or
c) tert-butoxy.

Particularly preferred compounds according to the invention of the formula (IV) are distinguished in that
G''' represents
a) tert-butoxy.

E' is a leaving group which is known or obvious to the person skilled in the art and which is described or mentioned, for example, in Synthese (1982), pages 85-125, Table 2, page 86; Carey and Sundberg, Organische Synthese, (1995), pages 279-281, Table 5.8; or Netscher, Recent Res. Dev. Org. Chem., 2003, 7, 71-83, schemes 1, 2, 10 and 15 or in Jerry March, Advanced Organic Chemistry, 4th edition, John Wiley and Sons, pp. 351-56 and 642-653), without being limited thereto.

Preferred compounds according to the invention of the general formula (III) are distinguished in that
E' represents
halogen or
sulphonyloxy.

Preferred halogens are iodo, bromo and chloro.

Preferred sulphonyloxy are methanesulphonyloxy, trifluoromethanesulphonyloxy, nonafluorobutyloxy, tosyloxy and nosyloxy.

Preferred compounds according to the invention of the general formula (IV) are distinguished in that
E' represents
a) chloro,
b) bromo,
c) methanesulphonyloxy,
d) trifluoromethanesulphonyloxy,
e) nonafluorobutyloxy,
f) tosyloxy or
g) iodo.

Preferred compounds according to the invention of the general formula (IV) are distinguished in that
E' represents
a) chloro,
b) bromo,
c) methanesulphonyloxy,
d) trifluoromethanesulphonyloxy,
e) nonafluorobutyloxy
f) tosyloxy or
g) iodo.

Preferred compounds according to the invention of the formula (IV) are distinguished in that
E' represents
a) bromo,
b) methanesulphonyloxy,
d) trifluoromethanesulphonyloxy, or
e) trifluoromesyloxy.

Further preferred compounds according to the invention of the formula (IV) are distinguished in that
E' represents
a) chloro,
b) bromo,
c) methanesulphonyloxy,
d) trifluoromethanesulphonyloxy,
e) tosyloxy or
f) iodo.

Particularly preferred compounds according to the invention of the formula (IV) are distinguished in that
E' represents
a) bromo or
b) methanesulphonyloxy.

Preferred compounds according to the invention of the formula (IV) are distinguished in that
Q' represents
a) N(H)-tert-butoxycarbonyl,
b) N(H)-benzyloxycarbonyl,
c) N(H)-trityl or d)
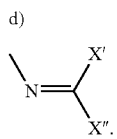

Further preferred compounds according to the invention of the formula (IV) are distinguished in that
Q' represents
a) N(H)-tert-butoxycarbonyl or b)
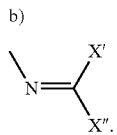

Preferred compounds according to the invention of the formula (IV) are distinguished in that
X' and X" independently of one another represent
a) branched or straight-chain $C_1$-$C_5$ alkyl,
b) substituted or unsubstituted aryl or
c) aralkyl.

Further preferred compounds according to the invention of the formula (IV) are distinguished in that
X' and X" independently of one another represent
a) branched or straight-chain $C_1$-$C_5$ alkyl or
b) substituted or unsubstituted aryl.

Particularly preferred compounds according to the invention of the formula (IV) are distinguished in that
X' and X" represent phenyl or phenyl which is substituted in the 2-position.

Particularly preferred compounds according to the invention of the formula (IV) are distinguished in that
$R^5$ and $R^6$ represent
a) hydrogen,
b) hydroxyl,
c) branched or straight-chain $C_1$-$C_5$ alkyl,
d) branched or straight-chain $C_1$-$C_5$ alkoxy or
e) $R^7$-E',
with the proviso that exactly one of the substituents $R^5$ or $R^6$ contains an E' and the respective other substituent contains no E', with the proviso that $R^5$ is not hydrogen.

Particularly preferred compounds according to the invention of the formula (IV) are distinguished in that
$R^5$ and $R^6$ represent
a) hydrogen,
b) hydroxyl,
c) branched or straight-chain $C_3$-$C_5$ alkyl,
d) branched or straight-chain $C_3$-$C_5$ alkoxy or
e) $R^7$-E', with the proviso that exactly one of the substituents $R^5$ or $R^6$ contains an E' and the respective other substituent contains no E', E' represents
a) chloro,
b) bromo,
c) mesyloxy,
d) trifluoromethylsulphonyloxy,
e) nonafluorobutyloxy,
f) tosyloxy or
g) iodo, $R^7$ represents
a) branched or straight-chain $C_1$-$C_5$ alkoxy,
b) branched or straight-chain $C_1$-$C_5$ alkyl,
c) branched or straight-chain $C_2$-$C_5$ alkenyl or
d) branched or straight-chain $C_2$-$C_5$ alkynyl.

Invention compounds of formula I, II and III are 2S glutamic acid or glutamine derivatives (L-glutamic acid or glutamine derivatives).

According to a further aspect, the present invention relates to an imaging kit comprising compounds of the general formula III or IV.

According to a further aspect, the present invention relates to pharmaceutical compositions comprising compounds of the general formula I, II, III or IV and suitable pharmaceutical carrier substances.

Compounds of the formula I or II are characterized in that the compounds are suitable for imaging in a dosage range of 37-600 MBq.

Preferred compounds of the formula I or II are characterized in that the compounds are particularly suitable in a dosage range of 150 MBq-370 MBq.

Compounds of the formula I or II for the use as medicament. Compounds of the formula I or II for use for the imaging in tumour disorders. Use of compounds of the formula I, II, III or IV for producing a medicament for the imaging in tumour disorders.

The process for preparing the compounds of the general formula (I) or (II) according to the invention is distinguished in that most of the compounds of the formula (I) or (II) can be formed by introducing the $^{18}F$ isotope into a compound of the general formula (IV).

The present invention relates to compounds of the general formula (IV).

Particularly preferred for introducing the $^{18}F$ isotope are 4,7,13,16,21,24-hexaoxa-1,10-diazabicyclo[8.8.8]hexacosane $K_{18}F$ (crone ether salt Kryptofix $K_{18}F$),
$K^{18}F$,
$H^{18}F$,
$KH^{18}F_2$,
$Cs^{18}F$,
$Na^{18}F$ or
$^{18}F$ tetraalkylammonium salt (for example [F-18]tetrabutylammonium fluoride).

The present invention relates to compounds of the general formula (I) or (II) and processes wherein the fluorine isotope $^{18}F$ is used.

If a compound of the formula (I), the formula (II), the formula (III), or the formula (IV) of the present subject matter of the invention contains one or more centres of chirality, the present invention embraces all forms of this isomer including all possible diastereomers, with the proviso that the substituent $R^1$-$R^6$ is present in S configuration. In cases where a carbon-carbon double bond is present, both the "cis" and "trans" isomer form part of the present invention. In cases where tautomeric forms may be present, such as, for example, keto-enol tautomerism, the present invention embraces all tautomeric forms, but these forms may be present in equilibrium or, preferably, in one form.

The compounds of the general formulae I and II and their preferred embodiments are used as medicaments.

The compounds of the general formula I or II according to the invention and their preferred embodiments are used in the diagnosis/imaging of physiological or pathological conditions.

These compounds are preferably used in the non-invasive PET-based diagnosis on the human or animal body.

Particularly preferably, the compounds of the general formula I or II according to the invention and their preferred embodiments are used in the diagnosis of tumour disorders. Examples of such tumour disorders are malignomas of the gastrointestinal or colorectal tract, liver carcinoma, pancreas carcinoma, kidney carcinoma, bladder carcinoma, thyroid carcinoma, prostrate carcinoma, endometrial carcinoma, ovary carcinoma, testes carcinoma, melanoma, small-cell and non-small-cell bronchial carcinoma, dysplastic oral mucosa carcinoma, invasive oral cancer; breast cancer, including hormone-dependent and hormone-independent breast cancer, squamous cell carcinoma, neurological cancer disorders including neuroblastoma, glioma, astrocytoma, osteosarcoma, meningioma, soft tissue sarcoma; haemangioma and endocrine tumours, including pituitary adenoma, chromocytoma, paraganglioma, haematological tumour disorders including lymphoma and leukaemias; or metastases of one of the tumours mentioned above.

The compounds of the general formula I or II according to the invention and their preferred embodiments are used for preparing a medicament for the diagnosis of tumour disorders. Examples of such tumour disorders are malignomas of the gastrointestinal or colorectal tract, liver carcinoma, pancreas carcinoma, kidney carcinoma, bladder carcinoma, thyroid carcinoma, prostrate carcinoma, endometrial carcinoma, ovary carcinoma, testes carcinoma, melanoma, small-cell and non-small-cell bronchial carcinoma, dysplastic oral mucosa carcinoma, invasive oral cancer; breast cancer, including hormone-dependent and hormone-independent breast cancer, squamous cell carcinoma, neurological cancer disorders including neuroblastoma, glioma, astrocytoma, osteosarcoma, meningioma, soft tissue sarcoma; haemangioma and endocrine tumours, including pituitary adenoma, chromocytoma, paraganglioma, haematological tumour disorders including lymphoma and leukaemias; or metastases of one of the tumours mentioned above.

The invention relates to pharmaceutical preparations comprising at least one compound of the formula I, II, III or IV and also a pharmaceutically acceptable carrier.

To the use of the compounds of the formula I, II, III or IV as medicaments, they are brought into the form of a pharmaceutical preparation which, in addition to the active compound, comprises pharmaceutical organic or inorganic inert carrier materials suitable for enteral or parenteral administration, such as, for example, water, gelatine, gum Arabic, lactose, starch, magnesium stearate, talcum, vegetable oils, polyalkylene glycols, etc.

The invention relates to a kit comprising at least one compound of the formula I, II, III, or IV.

The invention relates to the following embodiments:
Embodiment 1) Compounds of the general formula I

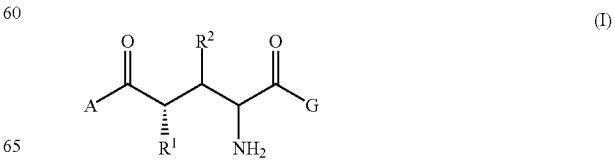

(I)

in which

A represents
a) hydroxyl,
b) branched or straight-chain $C_1$-$C_5$ alkoxy,
c) branched or straight-chain hydroxy $C_1$-$C_5$ alkoxy,
d) branched or straight-chain O—$C_1$-$C_5$ alkyl-(O—$C_1$-$C_4$ alkyl), —O—$C_1$-$C_4$ alkyl,
e) N($C_1$-$C_5$ alkyl)$_2$,
f) $NH_2$,
g) N(H)-L,
h) O-L or
i) O—Z, G represents
a) hydroxyl,
b) O—Z,
b) branched or straight-chain O—$C_1$-$C_5$ alkyl,
c) branched or straight-chain O—$C_2$-$C_5$ alkenyl,
d) branched or straight-chain O—$C_1$-$C_5$ alkyl-(O—$C_1$-$C_4$ alkyl), —O—$C_1$-$C_4$ alkyl,
e) branched or straight-chain O—$C_2$-$C_5$ alkynyl or
f) triphenylmethoxy, $R^1$ and $R^2$ represent
a) hydrogen,
b) branched or straight-chain $^{18}F$—$C_2$-$C_5$ alkoxy,
c) branched or straight-chain $^{18}F$—$C_1$-$C_5$ alkyl,
d) branched or straight-chain $^{18}F$—$C_2$-$C_5$ alkenyl,
e) branched or straight-chain $^{18}F$—$C_2$-$C_5$ alkynyl,
f) hydroxyl,
g) branched or straight-chain $C_1$-$C_5$ alkyl or
h) branched or straight-chain $C_1$-$C_5$ alkoxy, with the proviso that one of the substituents $R^1$ or $R^2$ contains exactly one $^{18}F$ isotope and the respective other substituent contains no $^{18}F$ isotope, with the proviso that $R^1$ is not hydrogen, L represents
a) branched or straight-chain $C_1$-$C_5$ alkyl,
b) branched or straight-chain $C_2$-$C_5$ alkenyl,
c) branched or straight-chain $C_1$-$C_5$ alkyl-(O—$C_1$-$C_4$ alkyl), —O—$C_1$-$C_4$ alkyl or
d) branched or straight-chain $C_2$-$C_5$ alkynyl, Z represents a metal cation equivalent, and
where n=0, 1, 2 or 3.

Embodiment 2) Compounds according to Embodiment 1, characterized in that A represents hydroxyl, branched or straight-chain $C_1$-$C_5$ alkoxy or $NH_2$.

Embodiment 3) Compound according to Embodiment 1 or 2, characterized in that A represents $NH_2$.

Embodiment 4) Compounds according to any of Embodiment 1 to 3, characterized in that $R^1$ is selected from the group consisting of $^{18}F$-methoxy, $^{18}F$-ethoxy, $^{18}F$-propoxy, $^{18}F$-ethyl and $^{18}F$-propyl, and $R^2$ is hydrogen.

Embodiment 5) Compound according to any of Embodiment 1 to 3, characterized in that $R^1$ represents $^{18}F$ and $R^2$ represents hydrogen.

Embodiment 6) Compound according to any of Embodiment 1 to 5, characterized in that G is selected from the group consisting of hydroxyl and branched or straight-chain O—$C_1$-$C_4$ alkyl.

Embodiment 7) Compound according to Embodiment 6, characterized in that G is methoxy.

Embodiment 8) Compound according to any of Embodiment 1 to 7, characterized in that Z is selected from the group consisting of $Mg^{2+}$, $Ca^{2+}$, $Na^+$ and K.

Embodiment 9) Compound according to Embodiment 1, selected from the group of compounds of the formulae:

a)

b)

c)

d)

e)

f)

Embodiment 10) Compounds of the general formula (II):

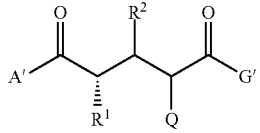

in which
A' represents
a) hydroxyl,
b) branched or straight-chain $C_1$-$C_5$ alkoxy,
c) branched or straight-chain hydroxy $C_1$-$C_5$ alkoxy,
d) branched or straight-chain O—$C_1$-$C_5$ alkyl-(O—$C_1$-$C_4$ alkyl), —O—$C_1$-$C_4$ alkyl,
e) N($C_1$-$C_5$ alkyl)$_2$,
f) $NH_2$,
g) N(H)-L',
h) O-L',
G' represents
a) hydroxyl,
b) O—Z',
c) branched or straight-chain O—$C_1$-$C_5$ alkyl,
d) branched or straight-chain O—$C_2$-$C_5$ alkenyl,
e) branched or straight-chain O—$C_1$-$C_5$ alkyl-(O—$C_1$-$C_4$ alkyl), —O—$C_1$-$C_4$ alkyl,
f) branched or straight-chain O—$C_2$-$C_5$ alkynyl or
g) triphenylmethoxy,
$R^1$ and $R^2$ represent
a) hydrogen,
i) branched or straight-chain $^{18}F$—$C_2$-$C_5$ alkoxy,
j) branched or straight-chain $^{18}F$—$C_1$-$C_5$ alkyl,
k) branched or straight-chain $^{18}F$—$C_2$-$C_5$ alkenyl,
l) branched or straight-chain $^{18}F$—$C_2$-$C_5$ alkynyl,
m) hydroxyl,
n) branched or straight-chain $C_1$-$C_5$ alkyl or
o) branched or straight-chain $C_1$-$C_5$ alkoxy,
with the proviso that exactly one of the substituents $R^1$ or $R^2$ contains exactly one $^{18}F$ isotope and the respective other substituent contains no $^{18}F$ isotope, with the proviso that $R^1$ is not hydrogen,
Q represents
a) N(H)-tert-butoxycarbonyl,
b) N(H)-allyloxycarbonyl,
c) N(H)-benzyloxycarbonyl,
d) N(H)-ethoxycarbonyl,
e) N(H)-methoxycarbonyl,
f) N(H)-propoxycarbonyl,
e) N(H)-2,2,2-trichloroethoxycarbonyl,
f) N(H)-1,1-dimethylpropynyl,
g) N(H)-1-methyl-1-phenylethoxycarbonyl,
h) N(H)-1-methyl-1-(4-biphenylyl)ethoxycarbonyl,
i) N(H)-cyclobutylcarbonyl,
j) N(H)-1-methylcyclobutylcarbonyl,
k) N(H)-vinylcarbonyl,
l) N(H)-allylcarbonyl,
m) N(H)-adamantylcarbonyl,
n) N(H)-diphenylmethylcarbonyl,
o) N(H)-cinnamylcarbonyl,
p) N(H)-formyl,
q) N(H)-benzoyl,
r) N(H)-trityl,
s) N(H)-p-methoxydiphenylmethyl,
t) N(H)-di(p-methoxyphenyl)phenylmethyl, u)

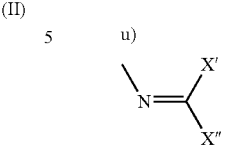

or
v) N-(tert-butoxycarbonyl)$_2$,
L' represents
a) branched or straight-chain $C_1$-$C_5$ alkyl,
b) branched or straight-chain $C_2$-$C_5$ alkenyl,
c) branched or straight-chain $C_1$-$C_5$ alkyl-(O—$C_1$-$C_4$ alkyl), —O—$C_1$-$C_4$ alkyl or
d) branched or straight-chain $C_2$-$C_5$ alkynyl,
X' and X" independently of one another represent
a) branched or straight-chain $C_1$-$C_5$ alkyl,
b) substituted or unsubstituted aryl,
c) substituted or unsubstituted aralkyl or
d) substituted or unsubstituted heteroaryl,
Z' represents a metal cation equivalent, and
where n=0, 1, 2 or 3.

Embodiment 11) Compounds according to Embodiment 10, characterized in that A' represents hydroxyl, branched or straight-chain $C_1$-$C_5$ alkoxy or $NH_2$.

Embodiment 12) Compounds according to Embodiment 11, characterized in that A' represents methoxy.

Embodiment 13) Compounds according to any of Embodiment 10 to 12, characterized in that $R^1$ is selected from the group consisting of $^{18}F$-ethoxy, $^{18}F$-propoxy, $^{18}F$-ethyl, and $^{18}F$-propyl, and $R^2$ is hydrogen.

Embodiment 14) Compound according to any of Embodiment 10 to 13, characterized in that G is selected from the group consisting of hydroxyl, and branched or straight-chain O—$C_1$-$C_4$ alkyl.

Embodiment 15) Compound according to Embodiment 14, characterized in that G represents methoxy.

Embodiment 16) Compound according to any of Embodiment 10 to 15, characterized in that Z' is selected from the group consisting of $Na^+$, $K^+$, $Ca^{2+}$ and $Mg^{2+}$.

Embodiment 17) Compound according to any of Embodiment 10 to 16, characterized in that Q is selected from the group consisting of N(H)-tert-butoxycarbonyl, N(H)-benzyloxycarbonyl and

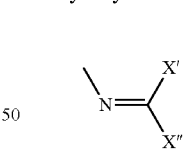

in which
X' and X" independently of one another represent
a) branched or straight-chain $C_1$-$C_5$ alkyl,
b) substituted or unsubstituted aryl,
c) substituted or unsubstituted aralkyl or
d) substituted or unsubstituted heteroaryl.

Embodiment 18) Compound according to Embodiment 17 characterized in that Q represents N(H)-tert-butoxycarbonyl.

Embodiment 19) Process for preparing compounds of the general formula (I) according to any of Embodiment 1 to 9, which comprises
removing one or more protective groups present in a compound of the formula (II) according to any of Embodiment 10 to 18.

Embodiment 20) Process for preparing compounds of the general formula (II) according to any of Embodiment 10 to 18,
which comprises
reacting a compound of the formula (III) according to Embodiment 24 with F-18 fluoride.
Embodiment 21) Compounds according to any of Embodiment 1 to 18 for use as medicaments.
Embodiment 22) Compounds according to any of Embodiment 1 to 18 for use for imaging in tumour disorders.
Embodiment 23) Use of compounds according to any of Embodiment 1 to 18 for preparing a medicament for imaging in tumour disorders.
Embodiment 24) Compounds of the formula (III)

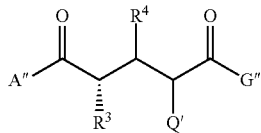

(III)

in which
A'' represents
a) branched or straight-chain $C_1$-$C_5$ alkoxy,
b) branched or straight-chain hydroxy $C_1$-$C_5$ alkoxy,
c) branched or straight-chain O—$C_1$-$C_5$ alkyl-(O—$C_1$-$C_4$ alkyl), —O—$C_1$-$C_4$ alkyl,
d) N($C_1$-$C_5$ alkyl)$_2$,
e) $NH_2$,
f) N(H)—U',
g) N(H)-L'', or
h) O-L'',
G'' represents
a) O—Z'',
b) branched or straight-chain O—$C_1$-$C_5$ alkyl,
c) branched or straight-chain O—$C_2$-$C_5$ alkenyl,
d) branched or straight-chain O—$C_1$-$C_5$ alkyl-(O—$C_1$-$C_4$ alkyl), —O—$C_1$-$C_4$ alkyl,
e) branched or straight-chain O—$C_2$-$C_5$ alkynyl or
f) triphenylmethoxy,
$R^3$ and $R^4$ represent
a) hydrogen,
b) branched or straight-chain E-$C_2$-$C_5$ alkoxy,
c) branched or straight-chain E-$C_1$-$C_5$ alkyl,
d) branched or straight-chain E-$C_2$-$C_5$ alkenyl,
e) branched or straight-chain E-$C_2$-$C_5$ alkynyl,
f) hydroxyl,
g) branched or straight-chain $C_1$-$C_5$ alkyl or
h) branched or straight-chain $C_1$-$C_5$ alkoxy,
with the proviso that exactly one of the substituents $R^3$ or $R^4$ contains an E and the respective other substituent contains no E, with the proviso that $R^3$ is not hydrogen,
E represents
a) chloro,
b) bromo,
c) methanesulphonyloxy,
d) trifluoromethylsulphonyloxy,
e) nonafluorobutyloxy,
f) tosyloxy or
g) iodo,
Q' represents
a) N(H)-tert-butoxycarbonyl,
b) N(H)-allyloxycarbonyl,
c) N(H)-benzyloxycarbonyl,
d) N(H)-ethoxycarbonyl,
e) N(H)-methoxycarbonyl,
f) N(H)-propoxycarbonyl,
g) N(H)-2,2,2-trichloroethoxycarbonyl,
h) N(H)-1,1-dimethylpropynyl,
i) N(H)-1-methyl-1-phenylethoxycarbonyl,
j) N(H)-1-methyl-1-(4-biphenylyl)ethoxycarbonyl,
k) N(H)-cyclobutylcarbonyl,
l) N(H)-1-methylcyclobutylcarbonyl,
m) N(H)-vinylcarbonyl,
n) N(H)-allylcarbonyl,
o) N(H)-adamantylcarbonyl,
p) N(H)-diphenylmethylcarbonyl,
q) N(H)-cinnamylcarbonyl,
r) N(H)-formyl,
s) N(H)-benzoyl,
t) N(H)-trityl,
u) N(H)-p-methoxydiphenylmethyl,
v) N(H)-di(p-methoxyphenyl)phenylmethyl, w)

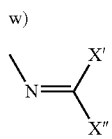

or
x) N-(tert-butoxycarbonyl)$_2$,
L'' represents
a) branched or straight-chain $C_1$-$C_5$ alkyl,
b) branched or straight-chain $C_2$-$C_5$ alkenyl,
c) branched or straight-chain $C_1$-$C_5$ alkyl-(O—$C_1$-$C_4$ alkyl), —O—$C_1$-$C_4$ alkyl or
d) branched or straight-chain $C_2$-$C_5$ alkynyl,
X' and X'' independently of one another represent
a) branched or straight-chain $C_1$-$C_5$ alkyl,
b) substituted or unsubstituted aryl,
c) substituted or unsubstituted alkylaryl or
d) substituted or unsubstituted heteroaryl,
Z'' represents a metal cation equivalent, and
where n=0, 1, 2 or 3.
Embodiment 25) Use of compounds of the formula (IV) for preparing compounds of the formula (I) or (II):

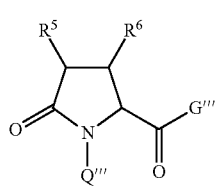

(IV)

in which
G''' represents
a) branched or straight-chain O—$C_1$-$C_5$ alkyl,
b) branched or straight-chain O—$C_2$-$C_5$ alkenyl,
c) branched or straight-chain O—$C_1$-$C_5$ alkyl-(O—$C_1$-$C_4$ alkyl), —O—$C_1$-$C_4$ alkyl,
d) branched or straight-chain O—$C_2$-$C_5$ alkynyl or
e) triphenylmethoxy,
$R^5$ and $R^6$ represent
a) hydrogen,
b) hydroxyl,
c) branched or straight-chain $C_1$-$C_5$ alkyl,
d) branched or straight-chain $C_1$-$C_5$ alkoxy or
e) $R^7$-E',
with the proviso that exactly one of the substituents $R^5$ or $R^6$ contains an E' and the respective other substituent contains no E', with the proviso that $R^5$ is not hydrogen, E' represents
a) chloro,
b) bromo,
c) methanesulphonyloxy,
d) trifluoromethanesulphonyloxy,
e) nonafluorobutyloxy,
f) tosyloxy or
g) iodo,
$R^7$ represents
a) branched or straight-chain $C_2$-$C_5$ alkoxy,
b) branched or straight-chain $C_1$-$C_5$ alkyl,
c) branched or straight-chain $C_2$-$C_5$ alkenyl or
d) branched or straight-chain $C_2$-$C_5$ alkynyl,
Q''' represents
a) N-tert-butoxycarbonyl
b) N-allyloxycarbonyl,
c) N-benzyloxycarbonyl,
d) N-ethoxycarbonyl,
e) N-methoxycarbonyl,
f) N-propoxycarbonyl,
g) N-2,2,2-trichloroethoxycarbonyl,
h) hydrogen,
i) N-1-methyl-1-phenylethoxycarbonyl,
j) N-1-methyl-1-(4-biphenylyl)ethoxycarbonyl,
k) N-cyclobutylcarbonyl,
l) N-1-methylcyclobutylcarbonyl,
m) N-vinylcarbonyl,
n) N-allylcarbonyl,
o) N-adamantylcarbonyl,
p) N-diphenylmethylcarbonyl,
q) N-cinnamylcarbonyl,
r) N-formyl,
s) N-benzoyl,
t) N(H)-trityl,
u) N(H)-p-methoxyphenyldiphenylmethyl,
v) N(H)-di(p-methoxyphenyl)phenylmethyl, w) 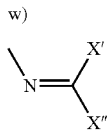

or
x) N-(tert-butoxycarbonyl)$_2$,
X' and X'' independently of one another represent
a) branched or straight-chain $C_1$-$C_5$ alkyl,
b) substituted or unsubstituted aryl,
c) substituted or unsubstituted alkylaryl or
d) substituted or unsubstituted heteroaryl, and
where n=0, 1, 2 or 3.

Embodiment 26) Imaging kit, comprising compounds of the general formula III or IV.

Embodiment 27) Pharmaceutical composition, comprising compounds of the general formula I, II, III or IV and suitable pharmaceutical carrier substances.

Embodiment 28) Compounds according to any of Embodiment 1 to 9, 10 to 18, and compounds of the general formula IV, characterized in that the compounds are suitable for imaging in a dosage range of 37-600 MBq.

Embodiment 29) Compounds according to Embodiment 28, characterized in that the compounds are particularly suitable in a dosage range of 150 MBq-370 MBq.

Compounds according to the invention in which the [F-18]-isotope is positioned via a methylene group in the 4-position of the glutamic acid skeleton, such as, for example, in 4S-[F-18]fluoromethylglutamic acid 1, can be prepared as shown in Scheme 7. Thus, for example, the acidic removal of the protective groups of the compound 2 affords the compound 4S-[F-18]fluoromethylglutamic acid 1 according to the invention.

Scheme 7

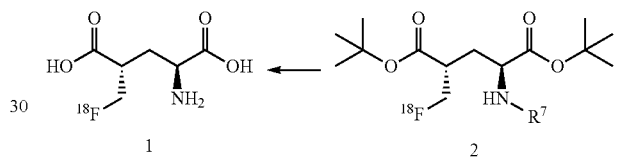

$R^7$ = protective group,
e.g. trityl, Boc, etc.

Here, various organic (for example trifluoroacetic acid), but especially inorganic acids, such as, for example, hydrobromic acid, hydrochloric acid, sulphuric acid, perchloric acid or phosphoric acid may be used. The compound 2 according to the invention of the formula (I) can be purified by HPLC, where, in principle, various purification steps may be carried out upstream or downstream, such as, for example, purification on a RP-C18 cartridge or other separating materials.

The radiochemical fluorination of tosylate 3, which is synthesized analogously to the method described in the literature (Chem. Pharm. Bull., 17, 5 (1969), 879-885) from 4 (Tetrahedron, 45, 5, (1989) 1453-1464), to the [F-18]-labelled glutamic acid derivative 2 can be carried out using methods known to the person skilled in the art (see Scheme 8).

Scheme 8

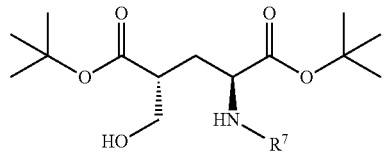

4

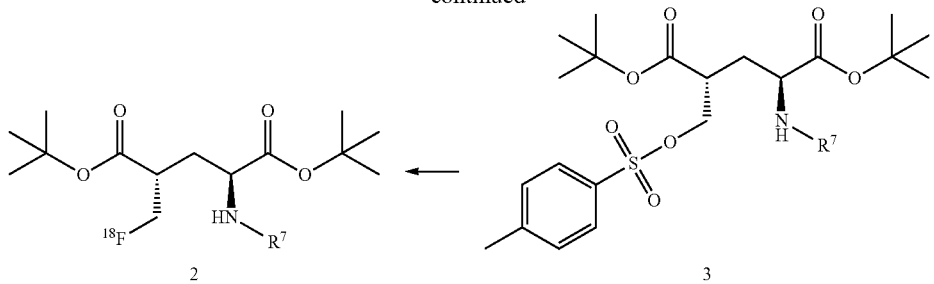

$R^7$ = protective group, e.g. trityl, Boc, etc.

Here, compound 3 can be reacted in the presence of a base, such as, for example, tetraalkylammonium carbonate and tetraalkylphosphonium carbonate and potassium carbonate, etc., with the appropriate [F-18]-fluoride solution. The reaction is preferably carried out at elevated temperatures. The addition of crone ethers, such as, for example, Kryptofix (K2.2.2), may have a positive effect on the reaction, in particular in combination with $K_2CO_3$ as catalyzing base. Possible solvents are preferably aprotic, but it is also possible to use protic solvents or else aprotic solvent additives, such as, for example, water. Usually, acetonitrile, dimethyl sulphoxide or dimethylformamide are used as the most suitable solvents for the radiochemical fluorination with [F-18]-fluoride anions. Usually, compound 2 does not have to be subjected to a purification but can be treated instantly using the methods described for the conversion of 2 into 1. However, a purification of the compound 2 is possible in principle, preferably using preparative HPLC with a nonpolar phase, such as, for example, RP C-18.

Compounds according to the invention in which the [F-18]-isotope is positioned via an alkoxy group in the 4S-configuration in the 4-position of the glutamic acid skeleton, such as, for example, in 4-S-(2-[F-18]fluoroethoxy-glutamic acid (5), can be prepared as shown in Scheme 9. Thus, for example, the acidic removal of the protective groups of the compound 6 or (7) affords the compound 4-S—[F-18] fluoroethoxyglutamic acid (5) according to the invention.

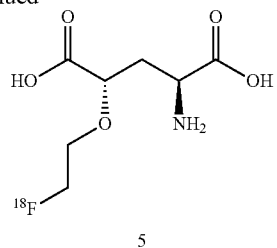

Here, various organic (for example trifluoroacetic acid), but especially inorganic acids, such as, for example, hydrobromic acid, hydrochloric acid, sulphuric acid, perchloric acid or phosphoric acid may be used. Also possible is a basic ring opening of 6 using lithium hydroxide, sodium hydroxide, potassium hydroxide, etc. (S. Baker et al. *Tetrahedron Lett.* 1998, 39, 2815-2818).

The compound 5 according to the invention of the formula (I) can be purified by HPLC, where, in principle, various purification steps may be carried out upstream or downstream, such as, for example, purification on a RP-C18 cartridge or other separating materials.

The radiochemical fluorination of tosylate 8, which is synthesized analogously to the method described in the literature (N. Sharma et al. *Tetrahedron Lett.* 2004, 45, 1403-1406) from 9, to the [F-18]-labelled S-glutamic acid derivative 6 can be carried out using methods known to the person skilled in the art (see Scheme 10).

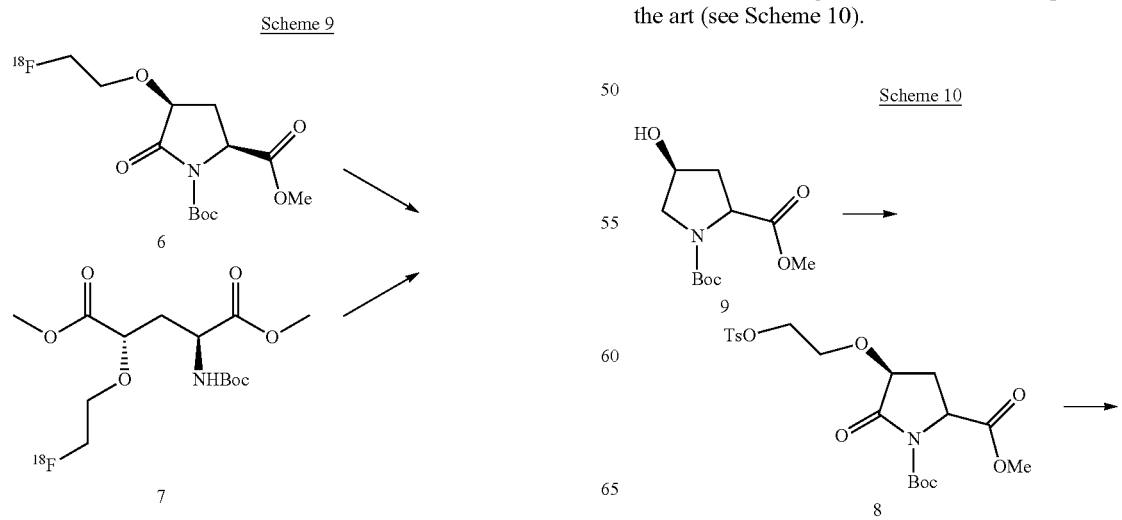

-continued

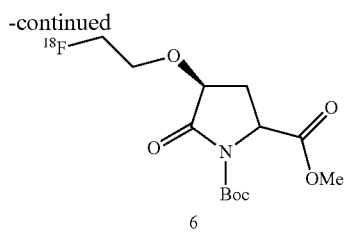
6

Here, compound 6 can be reacted in the presence of a base, such as, for example, tetraalkylammonium carbonate and tetraalkylphosphonium carbonate and potassium carbonate, etc., with the appropriate [F-18]-fluoride solution. The reaction is preferably carried out at elevated temperatures. The addition of crone ethers, such as, for example, Kryptofix (K2.2.2), may have a positive effect on the reaction, in particular in combination with $K_2CO_3$ as catalyzing base. Possible solvents are preferably aprotic, but it is also possible to use protic solvents or else aprotic solvent additives, such as, for example, water. Usually, acetonitrile, dimethyl sulphoxide or dimethylformamide are used as the most suitable solvents for the radiochemical fluorination with [F-18]-fluoride anions. Usually, compound 6 does not have to be subjected to a purification but can be treated instantly using the methods described for the conversion of 6 into 5. However, a purification of the compound 6 is possible in principle, preferably using preparative HPLC with a nonpolar phase, such as, for example, RP C-18. Also possible is a purification using cartridges.

The radiochemical fluorination of tosylate 10, which is synthesized analogously to the method described in the literature (X. Zhang *Tetrahedron Lett.* 2001, 42, 5335-5338) from 8, to the [F 18]-labelled glutamic acid derivative 7 can be carried out by methods known to the person skilled in the art (see Scheme 11).

Scheme 11

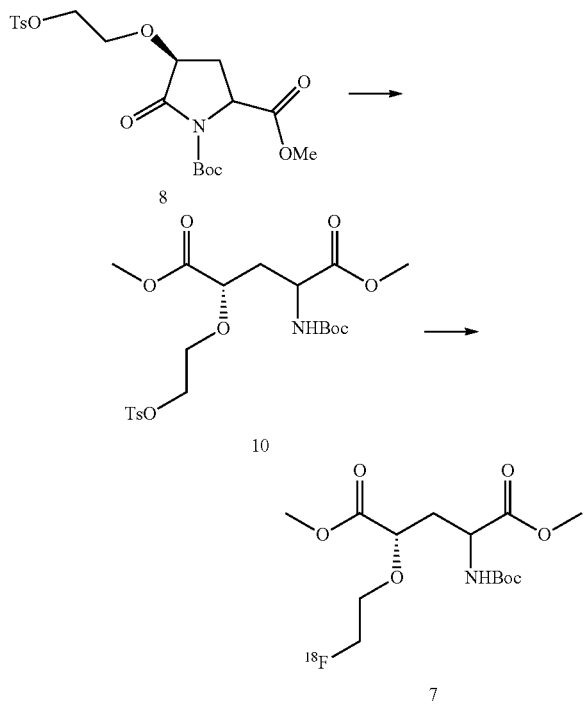

Here, compound 10 can be reacted in the presence of a base, such as, for example, tetraalkylammonium carbonate and tetraalkylphosphonium carbonate and potassium carbonate, etc., with the appropriate [F-18]-fluoride solution. The reaction is preferably carried out at elevated temperatures. The addition of crone ethers, such as, for example, Kryptofix (K2.2.2), may have a positive effect on the reaction, in particular in combination with $K_2CO_3$ as catalyzing base. Possible solvents are preferably aprotic, but it is also possible to use protic solvents or else aprotic solvent additives, such as, for example, water. Usually, acetonitrile, dimethyl sulphoxide or dimethylformamide are used as the most suitable solvents for the radiochemical fluorination with [F-18]-fluoride anions. Usually, compound 7 does not have to be subjected to a purification but can be treated instantly using the methods described for the conversion of 7 into 5. However, a purification of the compound 7 is possible in principle, preferably using preparative HPLC with a nonpolar phase, such as, for example, RP C-18. Also possible is a purification using cartridges.

Another suitable starting material for the radiochemical fluorination to 6 is the bromide 8a which can be obtained from 9 in two steps: by alkylation of 9 using 1,2-dibromoethane to give the bromoethoxypyrrolidine derivative 8b and subsequent oxidation using, for example, ruthenium(III) compounds, as described in Examples 3a and 3b.

Scheme 10a

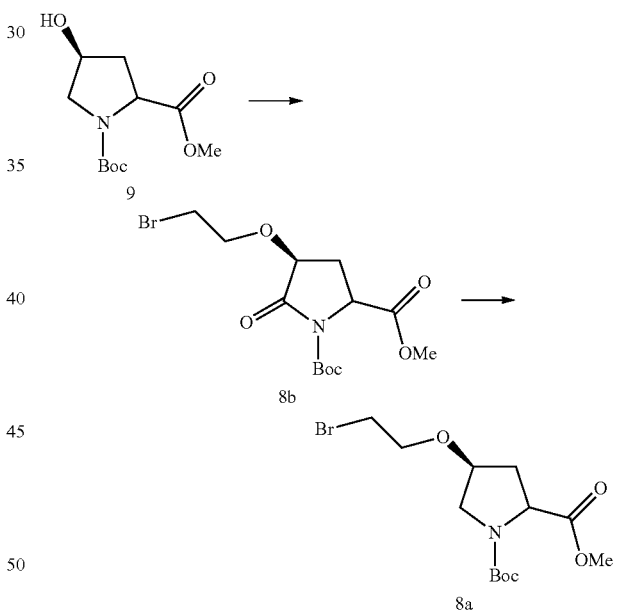

The synthesis of F-19 reference compounds 11, 12 and 13 can be carried out as shown in Scheme 12.

Scheme 12

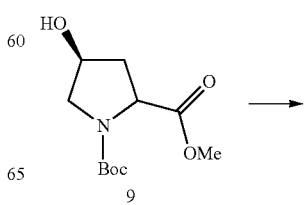
9

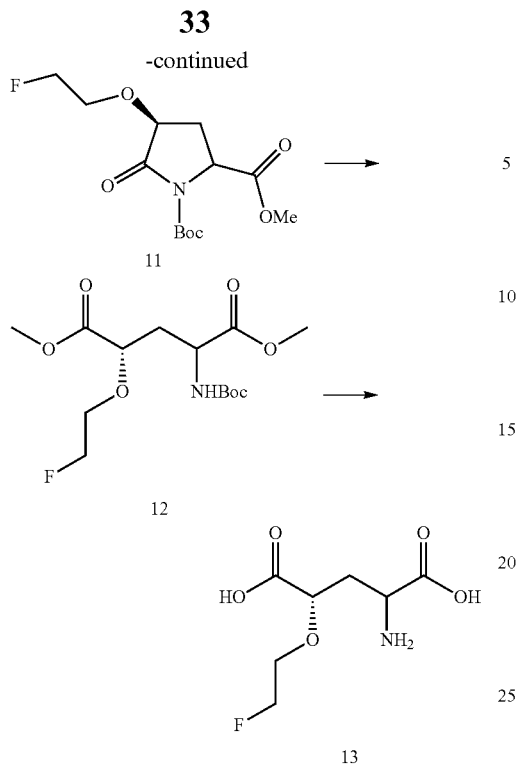

11 can be obtained by alkylating and oxidizing the hydroxyproline derivative 9. For preparing F-19 reference compounds, it has also been found to be advantageous to prepare the fluorides from analogous hydroxyl compounds using DAST (diethylaminosulphur trifluoride) according to methods known to the person skilled in the art, as described, for example, in Example 1d.

Ring-opening of the pyroglutamine derivative 26 gives the open-chain reference compound 12. The acidic removal of the protective groups leads to the glutamic acid derivative 13.

Compounds according to the invention in which the [F-18]-isotope is positioned via an alkyl group into the 4-position of the glutamic acid skeleton, such as, for example, 4-[F-18]fluoropropylglutamic acid 14 or 4-[F-18]fluorobutylglutamic acid 15, can be prepared as shown in Scheme 13. Thus, for example, the acidic removal of the protective groups of compounds 16 and 17 gives the compounds according to the invention 4-[F-18]fluoropropylglutamic acid 14 and 4-[F-18]fluorobutylglutamic acid 15, respectively.

Scheme 13

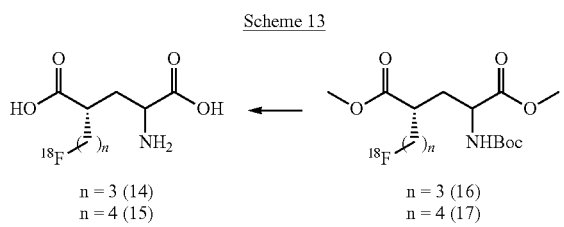

n = 3 (14)
n = 4 (15)

n = 3 (16)
n = 4 (17)

Here, various organic (for example trifluoroacetic acid), but especially inorganic acids, such as, for example, hydrobromic acid, hydrochloric acid, sulphuric acid, perchloric acid or phosphoric acid may be used. The compounds 14 and 15 according to the invention of the formula (I) can be purified by HPLC, where, in principle, various purification steps may be carried out upstream or downstream, such as, for example, purification using an RP-C18 cartridge or other separating materials.

The radiochemical fluorination of bromide 18 or tosylate 19, which are synthesized analogously to the method described in the literature (S. Hanessian, et al. *J. Org. Chem.* 2005, 70, 5070-5085) from 20, to the [F-18]-labelled glutamic acid derivatives 16 and 17 can be carried out by methods known to the person skilled in the art (see Scheme 14).

Scheme 14

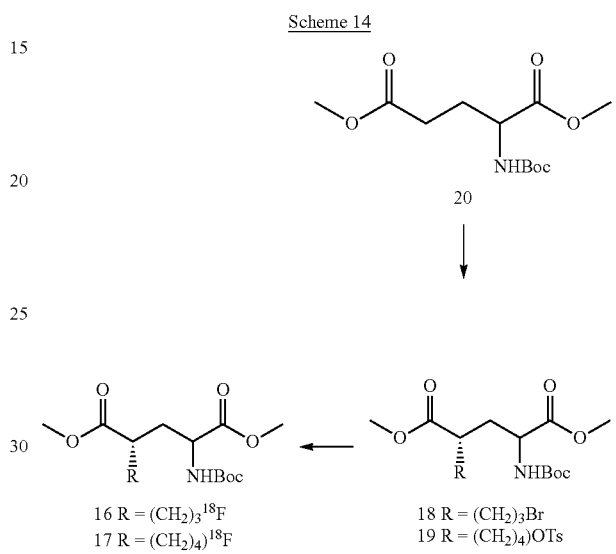

16 R = $(CH_2)_3{}^{18}F$
17 R = $(CH_2)_4{}^{18}F$

18 R = $(CH_2)_3Br$
19 R = $(CH_2)_4OTs$

Here, compounds 18 and 19 can be reacted in the presence of a base, such as, for example, tetraalkylammonium carbonate and tetraalkylphosphonium carbonate and potassium carbonate, etc., with the appropriate [F-18]-fluoride solution. The reaction is preferably carried out at elevated temperatures. The addition of crone ethers, such as, for example, Kryptofix (K2.2.2), may have a positive effect on the reaction, in particular in combination with $K_2CO_3$ as catalyzing base. Possible solvents are preferably aprotic, but it is also possible to use protic solvents or else aprotic solvent additives, such as, for example, water. Usually, acetonitrile, dimethyl sulphoxide or dimethylformamide are used as the most suitable solvents for the radiochemical fluorination with [F-18]-fluoride anions. Usually, compounds 16 and 17 do not have to be subjected to a purification but can be treated instantly using the methods described for the conversion of 16 into 14 or 17 into 15. However, a purification of the compounds 16 and 17 is possible in principle, preferably using preparative HPLC with a nonpolar phase, such as, for example, RP C-18.

The F-19 reference compounds 21 and 22 can be synthesized by alkylation of the glutamic acid derivative 20 (Scheme 15). Compound 20 can also be alkylated using iodides, preferably diiodides, analogously to Example 2a. In this case, a precursor suitable for radiochemical fluorination is obtained in one step from the commercially available glutamic acid derivative 20.

Scheme 15

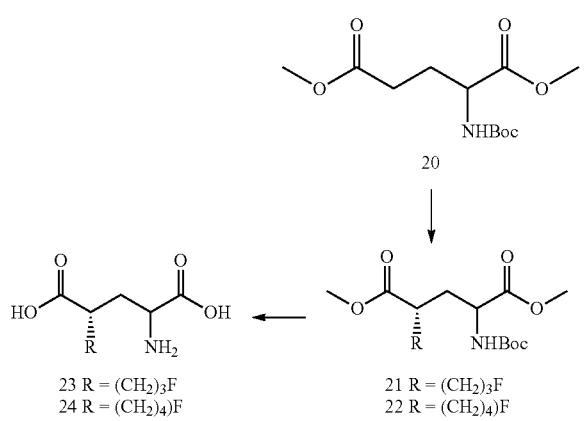

Removal of the protective groups affords the fluoroalkylated glutamic acid derivatives 23 and 24.

In each case, the C-3 or/and C4 position of a compound of the formula (I), the formula (II), the formula (III), the formula (IV) or the formula (V) of the present subject matter of the invention should contain the S-forms of the centres of chirality. In cases where a carbon-carbon double bond is present, both the "cis" and "trans" isomer form part of the present invention. In cases where tautomeric forms may be present, such as, for example, keto-enol tautomerism, the present invention embraces all tautomeric forms, but these forms may be present in equilibrium or, preferably, in one form.

The compounds of the general formulae I or II and their preferred embodiments are used as medicaments.

The compounds of the general formula I or II according to the invention and their preferred embodiments are used in the diagnosis of physiological or pathological conditions. These compounds are preferably used in the non-invasive PET-based diagnosis on the human or animal body.

Particularly preferably, the compounds of the general formula I or II according to the invention and their preferred embodiments are used in the diagnosis of tumour disorders. Examples of such tumour disorders are malignomas of the gastrointestinal or colorectal tract, liver carcinoma, pancreas carcinoma, kidney carcinoma, bladder carcinoma, thyroid carcinoma, prostrate carcinoma, endometrial carcinoma, ovary carcinoma, testes carcinoma, melanoma, small-cell and non-small-cell bronchial carcinoma, dysplastic oral mucosa carcinoma, invasive oral cancer; breast cancer, including hormone-dependent and hormone-independent breast cancer, squamous cell carcinoma, neurological cancer disorders including neuroblastoma, glioma, astrocytoma, osteosarcoma, meningioma, soft tissue sarcoma; haemangioma and endocrine tumours, including pituitary adenoma, chromocytoma, paraganglioma, haematological tumour disorders including lymphoma and leukaemias; or metastases of one of the tumours mentioned above.

The compounds of the general formula I or II according to the invention and their preferred embodiments are used for preparing a medicament for the diagnosis of tumour disorders. Examples of such tumour disorders are malignomas of the gastrointestinal or colorectal tract, liver carcinoma, pancreas carcinoma, kidney carcinoma, bladder carcinoma, thyroid carcinoma, prostrate carcinoma, endometrial carcinoma, ovary carcinoma, testes carcinoma, melanoma, small-cell and non-small-cell bronchial carcinoma, dysplastic oral mucosa carcinoma, invasive oral cancer; breast cancer, including hormone-dependent and hormone-independent breast cancer, squamous cell carcinoma, neurological cancer disorders including neuroblastoma, glioma, astrocytoma, osteosarcoma, meningioma, soft tissue sarcoma; haemangioma and endocrine tumours, including pituitary adenoma, chromocytoma, paraganglioma, haematological tumour disorders including lymphoma and leukaemias; or metastases of one of the tumours mentioned above.

The invention relates to pharmaceutical preparations comprising at least one compound of the formula I or II and also a pharmaceutically acceptable carrier.

To the use of the compounds of the formula I or II as medicaments, they are brought into the form of a pharmaceutical preparation which, in addition to the active compound, comprises pharmaceutical organic or inorganic inert carrier materials suitable for enteral or parenteral administration, such as, for example, water, gelatine, gum Arabic, lactose, starch, magnesium stearate, talcum, vegetable oils, polyalkylene glycols, etc.

The invention relates to a kit comprising at least one compound of the formula I, II, III, IV or V.

The term "aryl", used herein on its own or as part of another group, refers to mono- or bicyclic aromatic groups which may contain 6 to 10 carbon atoms in the ring, such as, for example, phenyl or naphthyl, and in which they may have any substitution. The aryl groups may be substituted in any suitable position leading to a stable compound, by one or more radicals from the group consisting of: hydroxyl, halogen, $C_1$-$C_5$-alkyl, $C_1$-$C_5$-alkoxy, cyano, $CF_3$, and nitro.

Substituents which may be mentioned are methoxy, ethoxy, propoxy, isopropoxy, hydroxyl, fluorine, chlorine, bromine, methyl, ethyl, propyl, isopropyl or trifluoromethyl groups.

In each case, halogen is to be understood as meaning fluorine, chlorine, bromine or iodine.

The term "alkyl", used herein on its own or as part of another group, refers to saturated carbon chains which may be straight-chain or branched, in particular to methyl, ethyl, n-propyl, isopropyl, n-butyl, isobutyl, tert-butyl or n-pentyl, 2,2-dimethylpropyl, 2-methylbutyl or 3-methylbutyl, n-hexyl, n-heptyl, n-octyl, n-nonyl or n-decyl groups. $C_1$-$C_{10}$-alkyl is optionally interrupted by one or more O, S or N The alkenyl substituents are in each case straight-chain or branched, including, for example, the following radicals: vinyl, propen-1-yl, propen-2-yl, but-1-en-1-yl, but-1-en-2-yl, but-2-en-1-yl, but-2-en-2-yl, 2-methylprop-2-en-1-yl, 2-methylprop-1-en-1-yl, but-1-en-3-yl, but-3-en-1-yl, allyl.

The alkynyl groups can be straight-chain or branched and are, for example, ethynyl, —CH$_2$—C≡CH, —CH$_2$—C≡CH, —C≡C—CH$_3$, —CH(CH$_3$)—C≡CH, —C≡C—CH$_2$(CH$_3$), —C(CH$_3$)$_2$C≡CH, —C≡C—CH(CH$_3$)$_2$—, —CH(CH$_3$)—C≡C—CH$_3$, —CH$_2$—C≡C—CH$_2$(CH$_3$).

Halogen represents fluoro, chloro, bromo and iodo. Preference is given to chloro, bromo and iodo.

The $C_1$-$C_5$-alkoxy groups can be straight-chain or branched and may represent a methoxy, ethoxy, n-propoxy, isopropoxy, n-butoxy, isobutoxy, tert-butoxy or n-pentoxy, 2,2-dimethylpropoxy, 2-methylbutoxy or 3-methylbutoxy group.

The heteroaryl radical comprises in each case 5-10 ring atoms and may, instead of a carbon atom, contain one or more identical or different heteroatoms, such as oxygen, nitrogen or sulphur, in the ring, and may additionally in each case be benzo-fused.

Examples which may be mentioned are:
thienyl, furanyl, pyrrolyl, oxazolyl, thiazolyl, imidazolyl, pyrazolyl, isoxazolyl, isothiazolyl, oxadiazolyl, triazolyl, thiadiazolyl, etc.
pyridyl, pyridazinyl, pyrimidinyl, pyrazinyl, triazinyl, etc.

EXAMPLES

Example 1

(2S,4S)-2-Amino-4-(3-fluoropropyl)pentanedioic acid a) Dimethyl (2S,4S)-4-allyl-2-tert-butoxycarbonyl-laminopentanedioate

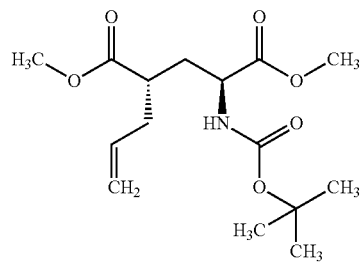 [SMILES: C=CC[C@@H](C[C@H](NC(=O)OC(C)(C)C)C(=O)OC)C(=O)OC]

11.01 g (40 mmol) of dimethyl Boc-glutamate (Advanced Chemtech) were dissolved in 160 ml of tetrahydrofuran and cooled to −70° C. 88 ml (88 mmol) of a 1M solution of lithium bis(trimethylsilyl)amide in tetrahydrofuran were added dropwise at this temperature over a period of one hour, and the mixture was stirred at −70° C. for another 2 hours. 14.52 g (120 mmol) of allylbromide were then added dropwise, and after 2 h at this temperature, the cooling bath was removed and 200 ml of 2N aqueous hydrochloric acid and 400 ml of ethyl acetate were added. The organic phase was separated off, washed with water until neutral, dried over sodium sulphate and filtered, and the filtrate was concentrated. The crude product obtained in this manner was chromatographed in silica gel using a hexane/ethyl acetate gradient, and the appropriate fractions were combined and concentrated.

Yield: 3.3 g (26.2%)
MS (ESIpos): m/z=316 [M+H]+
1H-NMR (400 MHz, CHLOROFORM-d): Shift [ppm]=1.44 (s, 9H), 1.99-2.02 (m, 2H), 2.31-2.39 (m, 2H), 2.56-2.61 (m, 1H), 3.67 (s, 3H), 3.73 (s, 3H), 4.33-4.15 (m, 1H), 4.33-4.37 (m, 1H), 4.95-4.97 (m, 1H), 5.04-5.10 (m, 2H), 5.67-5.76 (m, 1H).

b) Dimethyl (2S,4S)-2-tert-butoxycarbonylamino-4-(3-hydroxypropyl)pentanedioate

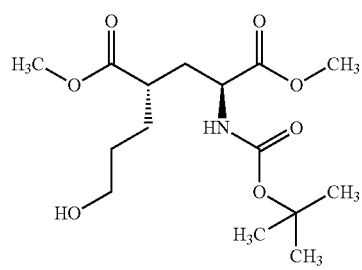 [SMILES: COC(=O)[C@@H](CCCO)C[C@H](NC(=O)OC(C)(C)C)C(=O)OC]

3.15 g (10 mmol) of the compound described in Example 1a were dissolved in 50 ml of tetrahydrofuran and cooled in an ice-bath. Over a period of about 20 minutes, 13.3 ml of 1 M diboran/tetrahydrofuran complex in tetrahydrofuran were added dropwise with ice-cooling and under nitrogen, and the mixture was stirred on ice for 1 h and at room temperature overnight. 15 ml of 1 N aqueous sodium hydroxide solution and 13.3 ml of 30% strength aqueous hydrogen peroxide solution were then added dropwise. After 30 minutes, the mixture was diluted with water, the tetrahydrofuran was distilled off and the remaining aqueous solution was extracted with ethyl acetate. The organic phase was separated off, washed with water until neutral, dried over sodium sulphate and filtered, and the filtrate was concentrated. The crude product obtained in this manner was chromatographed on silica gel using a hexane/ethyl acetate gradient, and the appropriate fractions were combined and concentrated.

Yield: 0.6 g (18%)
MS (ESIpos): m/z=334 [M+H]+
1H-NMR (600 MHz, CHLOROFORM-d): Shift [ppm]=1.44 (s, 9H), 1.47-1.98 (m, 6H), 2.51-2.55 (m, 1H), 3.61-3.62 (m, 2H), 3.68 (s, 3H), 3.74 (s, 3H), 4.37-4.41 (m, 1H), 5.04 (d, 1H).

c) Dimethyl (2S,4S)-2-tert-butoxycarbonylamino-4-(3-methanesulphonyloxypropyl)-pentanedioate

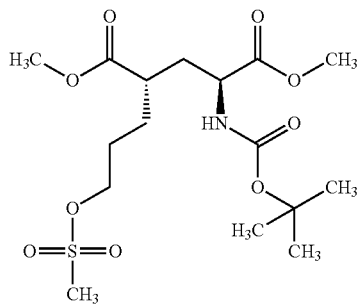 [SMILES: COC(=O)[C@@H](CCCOS(C)(=O)=O)C[C@H](NC(=O)OC(C)(C)C)C(=O)OC]

0.17 g (0.5 mmol) of the hydroxyl compound described in Example 1b was dissolved in dichloromethane and cooled in an ice-bath. After addition of 0.30 g (3 mmol) of triethylamine and 115 mg (1 mmol) of methanesulphonyl chloride, the mixture was stirred on ice for 2 h and then concentrated. The crude product obtained in this manner was chromatographed on silica gel using a hexane/ethyl acetate gradient and the appropriate fractions were combined and concentrated.

Yield: 145 mg (70.5%)
MS (ESIpos): m/z=412 [M+H]+
1H-NMR (300 MHz, CHLOROFORM-d): Shift [ppm]=1.44 (s, 9H), 1.68-1.79 (m, 4H), 1.98-2.05 (m, 2H), 2.48-2.56 (m, 1H), 3.02 (s, 3H), 3.69 (s, 3H), 3.74 (s, 3H), 4.20-4.24 (m, 2H), 4.30-4.39 (m, 1H), 4.95-4.99 (m, 1H).

d) Dimethyl (2S,4S)-2-tert-butoxycarbonylamino-4-(3-fluoropropyl)pentanedioate

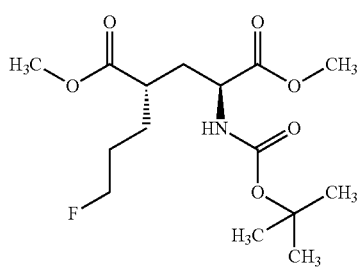 [SMILES: COC(=O)[C@@H](CCCF)C[C@H](NC(=O)OC(C)(C)C)C(=O)OC]

0.33 g (1 mmol) of the hydroxyl compound described in Example 1b was dissolved in 15 ml of dichloromethane and cooled on ice. After addition of 0.32 g (2 mmol) of diethylaminosulphur trifluoride (DAST), the mixture was stirred on ice for 1 h and then washed with water, the organic phase was dried over sodium sulphate and filtered and the filtrate was concentrated. The crude product obtained in this manner was chromatographed on silica gel using a dichloromethane/ethyl acetate gradient, and the appropriate fractions were combined and concentrated.

Yield: 25 mg (7.5%)
Elemental Analysis:

| calc. | C 53.72 | H 7.81 | F 5.66 | N 4.18 |
| found | C 53.55 | H 7.94 | F 5.21 | N 4.37 | e) (2S,4S)-2-Amino-4-(3-fluoropropyl)pentanedioic acid

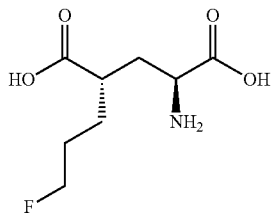

23.5 mg (0.07 mmol) of the compound described in Example 1d were dissolved in 2 ml of tetrahydrofuran, 1 ml of 1N aqueous sodium hydroxide solution was added and the mixture was stirred at room temperature for 4 h. The mixture was then concentrated to dryness, and the resulting crude product was dissolved in about 20 ml of 3N hydrogen chloride in diethyl ether, stirred overnight, concentrated and repeatedly coevaporated with diethyl ether. The crude product obtained in this manner was chromatographed on C18 silica gel using a water/methanol gradient, and the appropriate fractions were combined and concentrated.

Yield: 4 mg (27%)
Elemental analysis (calculated on the anhydrous compound):

| calc. | C 46.37 | H 6.81 | F 9.17 | N 6.76 |
| found | C 46.11 | H 7.02 | F 8.87 | N 6.93 | f) Dimethyl (2S,4S)-2-tert-butoxycarbonylamino-4-(3-[F-18]fluoropropyl)pentanedioate

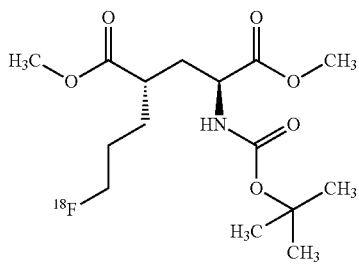 [SMILES: COC(=O)[C@@H](CCC[18F])C[C@H](NC(=O)OC(C)(C)C)C(=O)OC]

[F-18]-Fluoride was prepared by the [0-18](p,n)[F-18] reaction in a cyclotron. The isotope solution (4 GBq) was applied to a Sep-Pack Light QMA cartridge. The [F-18]-fluoride was eluted from the cartridge using a Kryptofix 2.2.2/potassium carbonate solution (5 mg K2.2.2, 1 mg potassium carbonate, acetonitrile (1.5 ml), water (0.5 ml). The solvent was removed at 120° C. in a stream of nitrogen with addition of acetonitrile (three times 1 ml).

5 mg (12.2 µmol) of dimethyl (2S,4S)-2-tert-butoxycarbonylamino-4-(3-methane-sulphonyloxypropyl)pentanedioate 1c in 1 ml of acetonitrile were added, and the resulting mixture was stirred at 110° C. for 10 min. After cooling to about 60° C., the mixture was passed through a Silica-Plus cartridge.

The intermediate was purified by HPLC (C18, acetonitrile/water. The HPLC fraction was diluted with water (about 50 ml) and passed through a C18 cartridge. The intermediate was eluted with 1 ml of acetonitrile. 940 MBq (39% d.c.) of dimethyl (2S,4S)-2-tert-butoxy-carbonylamino-4-(3-[F-18]fluoropropyl)pentanedioate if were obtained in a synthesis time of 80 min.

g) (2S,4S)-2-Amino-4-(3-[F-18]fluoropropyl)pentanedioic acid

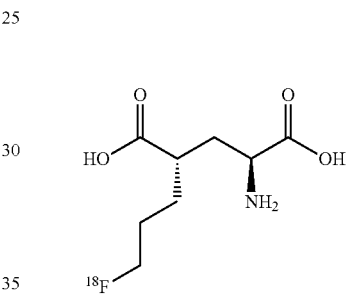

0.5 ml of 4N aqueous hydrochloric acid was added to 940 MBq of dimethyl 2-tert-butoxycarbonylamino-4-(3-[F-18]fluoropropyl)pentanedioate if in 1 ml of acetonitrile. With stirring, the mixture was heated at 130° C. (oil bath temperature) for 10 min. After cooling to room temperature, the solution was neutralized by addition of about 650 µl of 2N aqueous sodium hydroxide solution.

This gave 890 MBq (95% d.c.) of (2S,4S)-2-amino-4-(3-[F-18]fluoropropyl)pentanedioic acid 1g.

Example 2

(2S,4S)-2-Amino-4-(4-fluorobutyl)pentanedioic acid a) Dimethyl (2S,4S)-2-tert-butoxycarbonylamino-4-(4-iodobutyl)pentanedioate

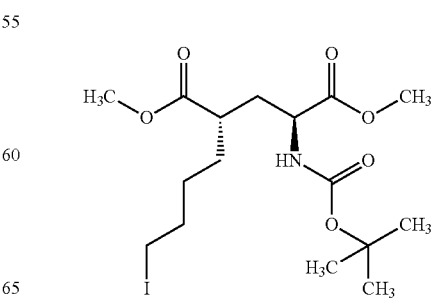

5.51 g (20 mmol) of dimethyl Boc-glutamate were dissolved in 60 ml of tetrahydrofuran and cooled to −70° C. Over a period of one hour, 44 ml (44 mmol) of a 1M solution of lithium bis(trimethylsilyl)amide in tetrahydrofuran were added dropwise at this temperature, and the mixture was stirred at −70° C. for 2 hours. 18.60 g (60 mmol) of 1,4-diiodobutane were then added dropwise, and after 2 h at this temperature the cooling bath is removed and 100 ml of 2N hydrochloric acid and 300 ml of ethyl acetate were added. The organic phase was separated off, washed with water until neutral, dried over sodium sulphate and filtered, and the filtrate was concentrated. The crude product obtained in this manner was chromatographed on silica gel using a hexane/ethyl acetate gradient, and the appropriate fractions were combined and concentrated.

Yield: 1.0 g (11.0%)
Elemental Analysis:

| calc.  | C 42.02 | H 6.17 | I 27.75 | N 3.06 |
|--------|---------|--------|---------|--------|
| found  | C 41.78 | H 6.30 | I 27.19 | N 3.22 | b) (2S,4S)-2-Amino-4-(4-fluorobutyl)pentanedioic acid

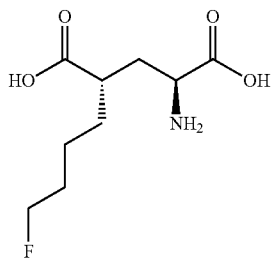

A solution of 152 mg (1.12 mmol) of silver fluoride in 1.5 ml of water was added to 0.45 g (1 mmol) of the compound described in Example 2a in 30 ml of acetonitrile, and the mixture was stirred at 40° C. overnight. The resulting suspension was filtered, the solution was evaporated to dryness and the crude product obtained in this manner was chromatographed on silica gel using a hexane/ethyl acetate gradient, and the appropriate fractions were combined and concentrated. The residue was dissolved in 20 ml of tetrahydrofuran, 10 ml of 1N aqueous sodium hydroxide solution were added and the mixture was stirred at room temperature for 4 h. The mixture was then concentrated to dryness, and the resulting crude product was dissolved in about 70 ml of 3N hydrogen chloride in diethyl ether, stirred overnight, concentrated and repeatedly coevaporated with diethyl ether. The resulting (2S,4S)-2-amino-4-(4-fluorobutyl)pentanedioic acid was chromatographed on C18 silica gel using a water/methanol gradient, and the appropriate fractions were combined and concentrated.

Yield: 33 mg (15%)
Elemental analysis (calculated on the anhydrous compound):

| calc.  | C 48.86 | H 7.29 | F 8.59 | N 6.33 |
|--------|---------|--------|--------|--------|
| found  | C 48.66 | H 7.55 | F 8.20 | N 6.57 | c) Dimethyl (2S,4S)-2-tert-butoxycarbonylamino-4-(4-[F-18]fluorobutyl)-pentanedioate

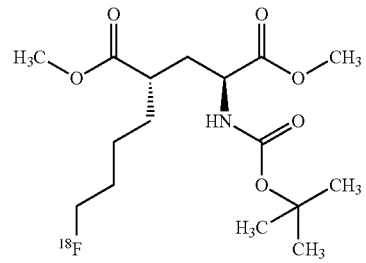 [SMILES: COC(=O)[C@@H](CCCC[18F])C[C@H](NC(=O)OC(C)(C)C)C(=O)OC]

[F-18]-Fluoride was prepared by the [O-18](p,n)[F-18] reaction in a cyclotron. The isotope solution (5.2 GBq) was applied to a Sep-Pack Light QMA cartridge. The [F-18]-fluoride was eluted from the cartridge using a Kryptofix 2.2.2/potassium carbonate solution (5 mg K2.2.2, 1 mg potassium carbonate, acetonitrile (1.5 ml), water (0.5 ml). The solvent was removed at 120° C. in a stream of nitrogen with addition of acetonitrile (three times 1 ml).

5 mg (10.9 µmol) of dimethyl (2S,4S)-2-tert-butoxycarbonylamino-4-(4-iodobutyl)pentanedioate 2a in 1 ml of acetonitrile were added, and the resulting mixture was stirred at 110° C. for 10 min. After cooling to about 60° C., the mixture was passed through a silica-plus cartridge.

The intermediate was purified by HPLC (C18, acetonitrile/water). The HPLC fraction was diluted with water (about 50 ml) and passed through a C18 cartridge. The intermediate was eluted with 1 ml of acetonitrile. 1.8 GBq (59% d.c.) of dimethyl (2S,4S)-2-tert-butoxycarbonylamino-4-(4-[F-18]fluorobutyl)pentanedioate 2c were obtained in a synthesis time of 85 min.

d) (2S,4S)-2-Amino-4-(4-[F-18]fluorobutyl)pentanedioic acid

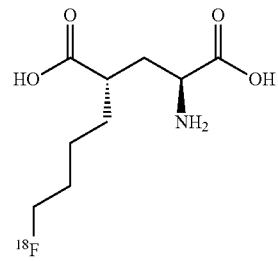 [SMILES: N[C@@H](C[C@H](CCCC[18F])C(=O)O)C(=O)O]

0.5 ml of 4N aqueous hydrochloric acid was added to 1.8 GBq of dimethyl 2(2S,4S)-2-tea-butoxycarbonylamino-4-(4-[F-18]fluorobutyl)pentanedioate 2c in 1 ml of acetonitrile. With stirring, the mixture was heated at 130° C. (oil bath temperature) for 10 min. After cooling to room temperature, the solution was neutralized by addition of about 700 µl of 2N aqueous sodium hydroxide solution.

This gave 1.7 GBq (94% d.c.) of (2S,4S)-2-amino-4-(4-[F-18]fluorobutyl)pentanedioic acid 2d.

Example 3

(2S,4S)-2-Amino-4-(2-fluoroethoxy)pentanedioic acid a) 1-tert-Butyl 2-methyl (2S,4S)-4-(2-bromoethoxy) pyrrolidine-1,2-dioate (precursor of 2-amino-4-(6-fluorohexyloxy)pentanedioic acid)

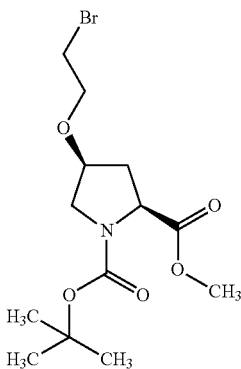 [SMILES: COC(=O)[C@@H]1C[C@H](OCCBr)CN1C(=O)OC(C)(C)C]

0.98 g (4 mmol) of 1-tert-butyl 2-methyl (2S,4S)-4-hydroxypyrrolidine-1,2-dioate (ALDRICH) was dissolved in 36 ml of 1,2-dibromoethane and cooled in an ice-bath. After addition of 1.36 g (4 mmol) of tetrabutylammonium bisulphite, 18 ml of 50% strength aqueous sodium hydroxide solution are added, and the mixture is stirred on ice for 2 hours and at room temperature overnight. After addition of 200 ml of water and 200 ml of dichloro-methane, the organic phase was washed once more with water, dried over sodium sulphate and filtered, and the filtrate was concentrated. The resulting crude product is chromatographed on silica gel using a dichloromethane/ethyl acetate gradient, and the appropriate fractions are combined and concentrated. Yield: 60 mg (4.3%)

Elemental Analysis:

| calc. | C 44.33 | H 6.30 | Br 22.69 | N 3.98 |
|---|---|---|---|---|
| found | C 44.02 | H 6.33 | Br 22.21 | N 4.11 | b) 1-tert-Butyl 2-methyl (2S,4S)-4-(2-bromoethoxy-5-oxopyrrolidine-1,2-dioate

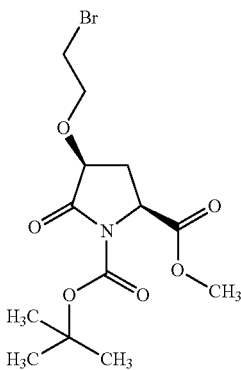 [SMILES: COC(=O)[C@@H]1C[C@H](OCCBr)C(=O)N1C(=O)OC(C)(C)C]

106 mg (0.3 mmol) of the compound described in Example 3a were dissolved in 10 ml of ethyl acetate. After addition of 14 mg (0.06 mmol) of ruthenium(III) chloride hydrate, a solution of 0.32 g (1.5 mmol) of sodium periodate in 4 ml of water was added, the mixture was stirred overnight and diluted with ethyl acetate, the organic phase was washed with water, dried over sodium sulphate and filtered and the filtrate was concentrated. The crude product obtained in this manner was chromatographed on silica gel using a hexane/ethyl acetate gradient, and the appropriate fractions were combined and concentrated.

Yield: 48 mg (43.7%)

Elemental Analysis:

| calc. | C 42.64 | H 5.50 | Br 21.82 | N 3.82 |
|---|---|---|---|---|
| found | C 42.33 | H 5.74 | Br 21.17 | N 3.59 | c) 1-tert-Butyl 2-methyl (2S,4S)-4-(2-fluoroethoxy)-5-oxopyrrolidine-1,2-dioate

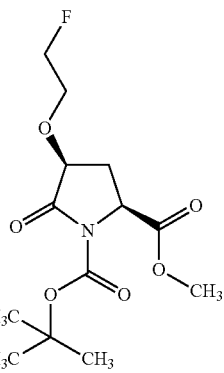

188 mg (0.5 mmol) of Kryptofix 222 and 29 mg (0.5 mmol) of potassium fluoride were added to 183 mg (0.5 mmol) of the compound described in Example 3b in 20 ml of dimethyl sulphoxide, and the mixture was reacted in a microwave oven at 100° C. for 30 minutes. The solution was concentrated under reduced pressure, the residue was partitioned between water and ethyl acetate, the ethyl acetate phase was washed with water, dried over sodium sulphate and filtered and the filtrate was concentrated. The crude product obtained in this manner was chromatographed on silica gel using a hexane/ethyl acetate gradient, and the appropriate fractions were combined and concentrated.

Yield: 13.7 mg (9.0%)

Elemental Analysis:

| calc. | C 51.14 | H 6.60 | F 6.22 | N 4.59 |
|---|---|---|---|---|
| found | C 50.84 | H 6.81 | F 6.00 | N 4.36 | d) (2S,4S)-2-Amino-4-(2-fluoroethoxy)pentanedioic acid

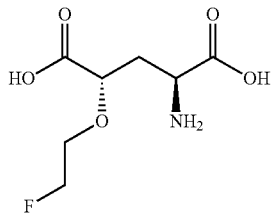

21.4 mg (0.07 mmol) of the compound described in Example 3c were dissolved in 2 ml of tetrahydrofuran, 1 ml of 1N aqueous sodium hydroxide solution was added and the mixture was stirred at room temperature for 4 h. The mixture is then evaporated to dryness, and the resulting crude product is suspended in about 20 ml of 6N aqueous hydrochloric acid, stirred at 80° C. for 6 h and concentrated. The crude product obtained in this manner was chromatographed on C18 silica gel using a water/methanol gradient, and the appropriate fractions were combined and concentrated.

Yield: 3.2 mg (22%)

Elemental Analysis (Calculated on the Anhydrous Compound):

| calc.: | C 40.19 | H 5.78 | F 9.08 | N 6.70 |
|---|---|---|---|---|
| found: | C 39.82 | H 5.86 | F 8.81 | N 6.96 | e) 1-tert-Butyl 2-methyl (2S,4S)-4-(2-[F-18]fluoroethoxy)-5-oxopyrrolidine-1,2-dioate

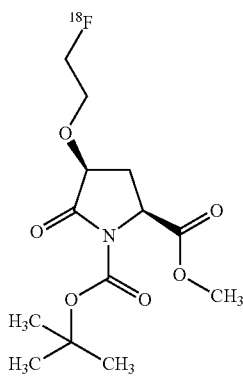 [SMILES: COC(=O)[C@@H]1C[C@H](OCC[18F])C(=O)N1C(=O)OC(C)(C)C]

[F-18]-Fluoride was prepared by the [O-18](p,n)[F-18] reaction in a cyclotron. The isotope solution (3.9 GBq) was applied to a Sep-Pack Light QMA cartridge. The [F-18]-fluoride was eluted from the cartridge using a Kryptofix 2.2.2/potassium carbonate solution (5 mg K2.2.2, 1 mg potassium carbonate, acetonitrile (1.5 ml), water (0.5 ml). The solvent was removed at 120° C. in a stream of nitrogen with addition of acetonitrile (three times 1 ml).

5 mg (13.7 μmol) of 1-tert-butyl 2-methyl (2S,4S)-4-(2-bromoethoxy)pyrrolidine-1,2-dioate 3a in 1 ml of acetonitrile were added, and the resulting mixture was stirred at 100° C. for 10 min. After cooling to about 70° C., the mixture was passed through a silica-plus cartridge. The intermediate was purified by HPLC (C18, acetonitrile/water). The HPLC fraction was diluted with water (about 50 ml) and passed through a C18 cartridge. The intermediate was eluted with 1 ml of acetonitrile. 1.3 GBq (52% d.c.) of 1-tert-butyl 2-methyl (2S,4S)-4-(2-[F-18]fluoroethoxy)-5-oxopyrrolidine-1,2-dioate 3e were obtained in a synthesis time of 70 min.

f) (2S,4S)-2-Amino-4-(2-[F-18]fluoroethoxy)pentanedioic acid

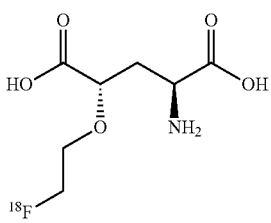 [SMILES: N[C@@H](C[C@H](OCC[18F])C(=O)O)C(=O)O]

0.5 ml of 4N aqueous hydrochloric acid was added to 1.3 GBq of 1-tert-butyl 2-methyl (2S,4S)-4-(2-[F-18]fluoroethoxy)-5-oxopyrrolidine-1,2-dioate 3e in 1 ml of acetonitrile. With stirring, the mixture was heated at 130° C. (oil bath temperature) for 10 min. After cooling to room temperature, the solution was neutralized by addition of about 700 μl of 2N aqueous sodium hydroxide solution.

This gave 1.2 GBq (92% d.c.) of (2S,4S)-2-amino-4-(2-fluoroethoxy)pentanedioic acid 3f.

Example 4

Cell Experiments

The uptake of the glutamic acid derivatives according to the invention into tumour cells was investigated in cell experiments. Here, the uptake of a radiolabelled glutamic acid derivative (4R/S-[F-18]F-L-glutamic acid) was examined in the presence of the compounds according to the invention and control substances (competition experiments). The compounds according to the invention were employed in excess (1 mM) over 4R/S-[F-18]F-L-glutamic acid (tracer).

Native L-configured glutamic acid (L-Glu), which, at a concentration of 1 mM L-Glu causes an 87% inhibition of tracer uptake in the assay, was used as positive control.

Surprisingly, it was found that 4S-configured methyl and hydroxy derivatives inhibit tracer uptake considerably better in each case than the corresponding 4R-configured derivatives. For the 4-hydroxy derivatives, competition values of 87% were determined for the S-configured derivative, whereas for the R-configured derivative, only 70% competition were determined. For the 4S-methyl derivative, even 92% inhibition were found whereas for the 4R-methyl derivative only 64% inhibition were found.

4S-(3-Fluoropropyl)-L-Glu showed a considerably better inhibition than other derivatives examined. Thus, 1 mM 4S-(3-fluoropropyl)-L-Glu was able to reduce tracer uptake by >94% to 5.4%.

TABLE 1

Examination of the biological activity of compounds according to the invention in the competition cell experiment. (A549 cells, 10 min of incubation with 0.250 MBq of 4R/S-[F-18]F-L-Glu in PBS buffer, competitor concentration 1 mM) (FIG. 1)

|  | % Tracer uptake | S.D. |
|---|---|---|
| Control | 100.0 | 3.5 |
| L-Glu | 12.6 | 1.6 |
| (4R/S)-fluoro-D/L-Glu | 16.3 | 2.5 |
| (4S)-hydroxy-L-Glu | 13.2 | 1.8 |
| (4R)-hydroxy-L-Glu | 29.6 | 4.2 |
| (4S)-methyl-L-Glu | 7.7 | 1.9 |
| (4R)-methyl-L-Glu | 33.5 | 5.5 |
| 4S-(3-fluoropropyl)-L-Glu | 5.4 | 2.2 |

Cell Uptake of S-Configured, F-18-Labelled Glutamic Acid Derivatives

Following labelling with F-18, (2S,4S)-2-amino-4-(3-[F-18]fluoropropyl)pentanedioic acid was examined in cell experiments with A549 and H460 tumour cells (both human non-small-cell bronchial carcinoma cell lines). Here, a time-dependent cellular uptake was observed.

After 30 min of incubation, it was possible to measure an uptake of 899 000 cpm per 100 000 cells for (2S,4S)-2-amino-4-(3-[F-18]fluoropropyl)pentanedioic acid. Accordingly, (2S,4S)-2-amino-4-(3-[F-18]fluoropropyl)pentanedioic acid accumulates to a greater degree in these tumour cells than the "Gold standard" [F-18]FDG after 30 minutes of incubation.

FIG. 2: time-dependent cellular uptake of (2S,4S)-2-amino-4-(3-[F-18]fluoropropyl)pentanedioic acid compared to [F-18]FDG. For all F-18-labelled compounds, a time-dependent intracellular radioactivity was observed. After 30 min, 840 000 cpm/~100 000 cells of (2S,4S)-2-amino-4-(3-[F-18]fluoropropyl)pentanedioic acid had been taken up. In the case of [F-18]FDG, 770 000 cpm/100 000 cells had been taken up after 30 min.

Animal Experiments (2S,4S)-2-Amino-4-(3-[F-18]fluoropropyl)pentanedioic acid was studied in mice bearing A549 tumours in an organ distribution experiment. (Table 2)

0.25 h after injection, 2.4% of the injected dose per g (% ID/g) was measured in the tumour, after 1 h, the tumour uptake is 1.6% ID/g. A transient uptake or excretions were observed in the kidneys and the pancreas. Thus, after 0.25 h, an uptake of 14.4% ID/g and 13.6% ID/g, respectively, was observed in these organs. After 1 h, the activity in these organs was reduced to 2% ID/g and 4% ID/g, respectively.

At all points in time, the uptake into the bones was <0.5% ID/g.

TABLE 2

Organ distribution after i.v. administration of 250 kBq of (2S,4S)-2-amino-4-(3-[F-18]fluoropropyl)pentanedioic acid (F-18 FSPG) in mice bearing A549 tumours.

| | Time | | | | | | | |
|---|---|---|---|---|---|---|---|---|
| | 0.25 h | | 0.5 h | | 1.0 h | | 2.00 h | |
| % dose/g | | S.D. | | S.D. | | S.D. | | S.D. |
| spleen | 2.87 | 0.11 | 1.76 | 0.38 | 1.02 | 0.07 | 0.53 | 0.13 |
| liver | 0.55 | 0.11 | 0.46 | 0.12 | 0.21 | 0.03 | 0.11 | 0.03 |
| kidney | 14.38 | 4.41 | 6.44 | 0.71 | 2.01 | 0.17 | 0.80 | 0.17 |
| lung | 1.35 | 0.03 | 1.08 | 0.19 | 0.50 | 0.08 | 0.29 | 0.02 |
| bone | 0.44 | 0.06 | 0.37 | 0.07 | 0.20 | 0.03 | 0.20 | 0.03 |
| heart | 0.42 | 0.08 | 0.20 | 0.02 | 0.08 | 0.01 | 0.05 | 0.00 |
| brain | 0.09 | 0.01 | 0.10 | 0.05 | 0.06 | 0.01 | 0.05 | 0.01 |
| fat | 0.31 | 0.30 | 0.08 | 0.03 | 0.04 | 0.01 | 0.09 | 0.11 |
| thyroid | 1.17 | 0.33 | 1.31 | 0.55 | 0.77 | 0.24 | 0.42 | 0.10 |
| muscle | 0.17 | 0.03 | 0.09 | 0.00 | 0.05 | 0.00 | 0.03 | 0.00 |
| tumour | 2.42 | 0.39 | 1.82 | 0.21 | 1.58 | 0.15 | 0.97 | 0.21 |
| skin | 1.71 | 0.20 | 2.26 | 0.64 | 1.80 | 0.04 | 1.01 | 0.10 |
| blood | 0.72 | 0.12 | 0.35 | 0.06 | 0.13 | 0.01 | 0.07 | 0.01 |
| tail | 2.74 | 0.34 | 3.45 | 1.86 | 1.19 | 0.13 | 1.69 | 0.60 |
| stomach | 3.25 | 0.27 | 2.64 | 0.70 | 0.96 | 0.29 | 0.39 | 0.09 |
| ovary | 1.82 | 0.29 | 1.13 | 0.48 | 0.94 | 0.56 | 0.28 | 0.20 |
| uterus | 1.30 | 0.47 | 1.27 | 0.74 | 0.93 | 0.44 | 0.37 | 0.33 |
| intestine | 1.27 | 0.06 | 0.90 | 0.28 | 0.52 | 0.06 | 0.32 | 0.07 |
| pancreas | 13.64 | 0.59 | 8.51 | 0.65 | 3.99 | 0.66 | 1.35 | 0.15 |
| adrenals | 0.94 | 0.23 | 0.78 | 0.38 | 0.27 | 0.11 | 0.20 | 0.04 |

PET/CT Imaging with (2S,4S)-2-amino-4-(3-[F-18]fluoropropyl)pentanedioic acid in Mice Bearing A549 Tumours 60 min after i.v. administration of 10 MBq of (2S,4S)-2-amino-4-(3-[F-18]fluoropropyl)pentanedioic acid to mice carrying A549 tumours, a 20 min data acquisition using a PET/CT scanner (Inveon) was started. Image analysis shows a high uptake of (2S,4S)-2-amino-4-(3-[F-18]fluoropropyl)pentanedioic acid into the A549 tumour.

PET with (4S)-4-(3-[F-18]fluoropropyl)-L-Glu with Rats Bearing H460 Tumours 80 min after i.v. administration of 18 MBq of (2S,4S)-2-amino-4-(3-[F-18]fluoropropyl)pentanedioic acid in rats bearing H460 tumours, a 20 min data acquisition with a PET scanner (Inveon) was started. Image analysis shows a high uptake of (2S,4S)-2-amino-4-(3-[F-18]fluoropropyl)pentanedioic acid into the H460 tumour.

FIG. 3. PET/CT study with (2S,4S)-2-amino-4-(3-[F-18]fluoropropyl)pentanedioic acid in mice bearing A549 tumours (to the left, section image analyses, to the right, maximum intensity projection, 90 min. after i.v. administration of 10 MBq (4S)-4-(3-[F-18]fluoropropyl)-L-Glu)

FIG. 4. PET with (2S,4S)-2-amino-4-(3-[F-18]fluoropropyl)pentanedioic acid in rats bearing H460 tumours (section image analysis, 80-100 min after i.v. administration of 16 MBq of (4S)-4-(3-[F-18]fluoropropyl)-L-Glu)

FIG. 5. PET with (2S,4S)-2-amino-4-(3-[F-18]fluoropropyl)pentanedioic acid in rats bearing H460 tumours (maximum intensity projection, 80-100 min after i.v. administration of 16 MBq of (2S,4S)-2-amino-4-(3-[F-18]fluoropropyl) pentanedioic acid.

Example 5

(2S,4S)-2-Amino-4-(3-[F-18]fluoropropyl)-pentanedioate a) di-tert-butyl (2S,4S)-4-allyl-2-tert-butoxycarbonylamino-pentanedioate

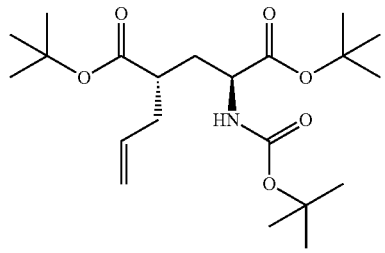 [SMILES: C=CC[C@@H](C[C@H](NC(=O)OC(C)(C)C)C(=O)OC(C)(C)C)C(=O)OC(C)(C)C]

26.96 g (75 mmol) of di-tert-butyl Boc-glutamate (Journal of Peptide Research (2001), 58, 338) were dissolved in 220 mL of tetrahydrofuran (THF) and cooled to −70° C. 165 mL (165 mmol) of a 1M solution of lithium bis(trimethylsilyl) amide in THF were added dropwise over a period of two hours at this temperature and the mixture was stirred at −70° C. for another 2 hours. 27.22 g (225 mmol) of allyl bromide were then added dropwise, and after 2 h at this temperature, the cooling bath was removed and 375 mL of 2N aqueous hydrochloric acid and 1.25 L of ethyl acetate were added. The organic phase was separated off, washed with water until neutral, dried over sodium sulphate and filtered, and the filtrate was concentrated. The crude product obtained in this manner was chromatographed in silica gel using a hexane/ethyl acetate gradient, and the appropriate fractions were combined and concentrated.

Yield: 15.9 g (53.1%)

MS (ESIpos): m/z=400 [M+H]$^+$

1H NMR (300 MHz, CHLOROFORM-d) d ppm 1.32-1.58 (m, 27H) 1.81-1.92 (m, 2H) 2.25-2.39 (m, 2H) 2.40-2.48 (m, 1H), 4.10-4.18 (m, 1H) 4.85-4.92 (d, 1H) 5.02-5.11 (m, 2H) 5.68-5.77 (m, 1H)

b) di-tert-butyl (2S,4S)-2-tert-butoxycarbonylamino-4-(3-hydroxypropyl)-pentanedioate

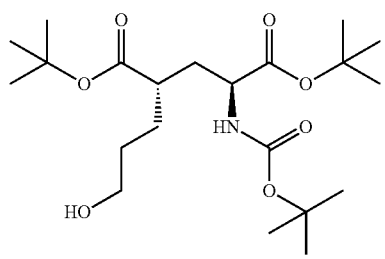 [SMILES: CC(C)(C)OC(=O)N[C@@H](C[C@H](CCCO)C(=O)OC(C)(C)C)C(=O)OC(C)(C)C]

15.58 g (39 mmol) of di-tert-butyl (2S,4S)-4-allyl-2-tert-butoxycarbonylamino-pentanedioate 5a were dissolved in 200 mL of tetrahydrofuran (THF) and cooled in an ice-bath. Over a period of about 20 minutes, 54.6 mL (54.6 mmol) of 1 M diboran/tetrahydrofuran complex in tetrahydrofuran were added dropwise with ice-cooling and under nitrogen, and the mixture was stirred on ice for 2 h and at room temperature overnight. It was cooled again to 0° C. and 58.5 mL of 1 N aqueous sodium hydroxide solution and 58.5 mL of 30% aqueous hydrogen peroxide solution were then added dropwise. After 60 minutes, the mixture was diluted with water, the tetrahydrofuran was distilled off and the remaining aqueous solution was extracted with ethyl acetate. The organic phase was separated off, washed with water until neutral, dried over sodium sulphate and filtered, and the filtrate was concentrated. The crude product obtained in this manner was chromatographed on silica gel using a hexane/ethyl acetate gradient, and the appropriate fractions were combined and concentrated.

Yield: 8.5 g (52.2%)

MS (ESIpos): m/z=418 [m+H]$^+$

1H NMR (300 MHz, CHLOROFORM-d) d ppm 1.32-1.58 (m, 27H) 1.60-1.70 (m, 2H) 1.73-1.94 (m, 4H) 2.05-2.12 (m, 1H), 2.33-2.40 (m, 1H) 3.58-3.68 (m, 2H) 4.15-4.22 (m, 1H) 4.95-5.03 (d, 1H)

c) di-tert-butyl (2S,4S)-2-tert-butoxycarbonylamino-4-(3-nitrophenylsulfonyloxy-propyl)-pentanedioate

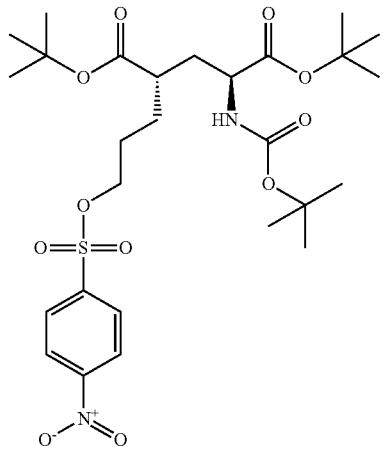 [SMILES: CC(C)(C)OC(=O)N[C@@H](C[C@H](CCCOS(=O)(=O)c1ccc([N+](=O)[O-])cc1)C(=O)OC(C)(C)C)C(=O)OC(C)(C)C]

5.22 g (12.5 mmol) of di-tert-butyl (2S,4S)-2-tert-butoxycarbonylamino-4-(3-hydroxypropyl)-pentanedioate 5b were dissolved in 125 mL of dichloromethane and cooled in an ice-bath. After addition of 7.59 g (75 mmol) of triethylamine and 5.54 g (25 mmol) nitrophenylsulphonyl chloride, the mixture was stirred on ice for 2 h and then concentrated. The crude product obtained in this manner was chromatographed on silica gel using a hexane/ethyl acetate gradient and the appropriate fractions were combined and concentrated.

Yield: 4.7 g (62.4%)

MS (ESIpos): m/z=603 [m+H]$^+$

1H NMR (300 MHz, CHLOROFORM-d) d ppm 1.42-1.45 (m, 27H) 1.57-1.87 (m, 6H) 2.29 (m, 1H) 4.01 (m, 1H) 4.13-4.16 (m, 2H) 4.86 (d, 1H) 8.12 (d, 2H) 8.42 (d, 2H)

d) di-tert-butyl (2S,4S)-2-tert-butoxycarbonylamino-4-(3-fluoropropyl)-pentanedioate

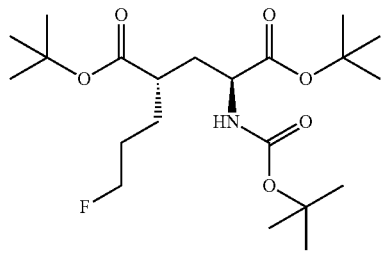 [SMILES: CC(C)(C)OC(=O)N[C@@H](C[C@H](CCCF)C(=O)OC(C)(C)C)C(=O)OC(C)(C)C]

29.22 g (70 mmol) of the hydroxyl compound described in Example 5b were dissolved in 700 mL of tetrahydrofuran (THF) and then 42.5 g (420 mmol) triethylamine was added. After addition of 25.14 g (140 mmol) of perfluorbutanefluoride acid (Aldrich) and 22.57 g (140 mmol) triethylamine/fluorohydroxyde (Aldrich), the mixture was stirred at room temperature 65 h, was concentrated and the crude product obtained in this manner was chromatographed in silica gel using a hexane/ethyl acetate gradient, and the appropriate fractions were purified and concentrated.

Yield: 15.9 g (54.1%)

MS (ESIpos): m/z=420 [m+H]$^+$

1H NMR (300 MHz, CHLOROFORM-d) d ppm 1.40-1.55 (m, 27H) 1.60-1.95 (m, 6H) 2.33-2.42 (m, 1H) 4.15-4.22 (m, 1H) 4.30-4.40 (m, 1H) 4.48-4.55 (m, 1H) 4.85-4.90 (d, 1H)

e) (2S,4S)-2-Amino-4-(3-fluoropropyl)-pentanedioate

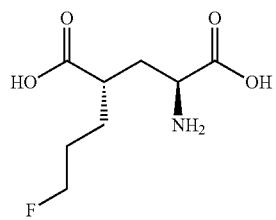

15.52 g (37 mmol) of the example 5d were dissolved gently in 110 mL Trifluoroacid and 3 days at room temperature stirred. The mixture was concentrated by drying and the crude product obtained in this manner was distilled 3 times with Diethylether and the rest was dissolved in around 200 mL water, with 20 mL 1N Salzsäure of pH 2, and washed with Dichloromethane and Ethylacetate subsequently and the solution was placed at a pH 7.4. with a 1 N sodium salt (ca. 65 mL) auf pH 7.4. the solution was dry-frozen and then was chromatographed in silica gel using a hexane/ethyl acetate gradient, and the appropriate fractions were purified and concentrated.

Yield: 7.5 g (88%)

MS (ESIpos): m/z=208 [M+H]+

1H NMR (300 MHz, methanol-d) d ppm 1.62-1.87 (m, 5H) 2.11 (m, 1H) 2.47-2.52 (m, 1H) 3.45 (m, 1H) 4.41 (m, 2H)

f) di-tert-butyl (2S,4S)-2-tert-Butoxycarbonylamino-4-(3-[F-18]fluorpropyl)-pentanedioate

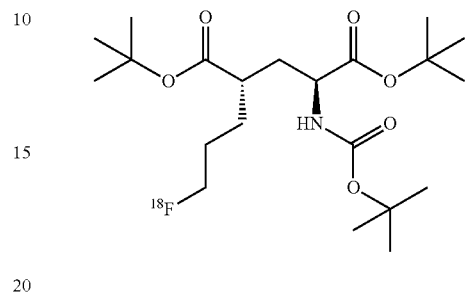

[F-18]-Fluoride was prepared by the [O-18](p,n)[F-18] reaction in a cyclotron. The isotope solution (3.5 GBq) was applied to a Sep-Pack Light QMA cartridge. The [F-18]-fluoride was eluted from the cartridge using a Kryptofix 2.2.2/potassium carbonate solution (5 mg K2.2.2, 1 mg potassium carbonate, acetonitrile (1.5 ml), water (0.5 ml). The solvent was removed at 120° C. in a stream of nitrogen with addition of acetonitrile (three times 1 ml).

5 mg (8.3 µmol) di-tert-butyl ester (2S,4S)-2-tert-Butoxycarbonylamino-4-(3-[4-Nitrobenzenesulfonyloxy-propyl)-pentanedioate 5c in 1 mL Acetonitrile were added, and the resulting mixture was stirred at 110° C. for 10 min. After cooling to about 60° C., the mixture was passed through a silica-plus cartridge.

The intermediate was purified by HPLC (C18, acetonitrile/water). The HPLC fraction was diluted with water (about 50 ml) and passed through a C18 cartridge. The intermediate was eluted with 1 ml of acetonitrile. 970 MBq (46% d.c.) of di-t-butyl ester (2S,4S)-2-tea-Butoxycarbonylamino-4-(3-[F-18]fluoropropyl)-pentanedioate 5f were obtained in a synthesis time of 80 min.

h) (2S,4S)-2-Amino-4-(3-[F-18]fluoropropyl)-pentanedioate

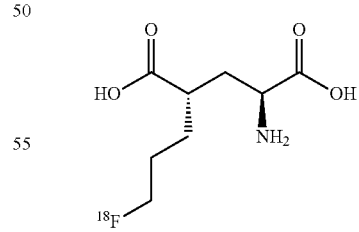

960 MBq of di-tert-butyl (2S,4S)$_2$-tert-Butoxycarbonylamino-4-(3-[F-18]fluoropropyl)-pentanedioate 5f in 1 mL Acetonitrile were with 0.5 mL 4N HCl versetzt. The mixture was stirred 10 min at the heated temperature of 130° C. (oil bath temperature). After cooling to room temperature, the solution was neutralised with the addition of around 650 µL 2N NaOH.

This gave 920 MBq (97% d.c.) of (2S,4S)-2-amino-4-(3-fluoropropyl)pentanedioate.

Beispiel 6 di-tert-butyl (2S,4S)-2-tert-Butoxycarbonylamino-4-(3-p-toluolsulfonyloxy-propyl)-pentanediote

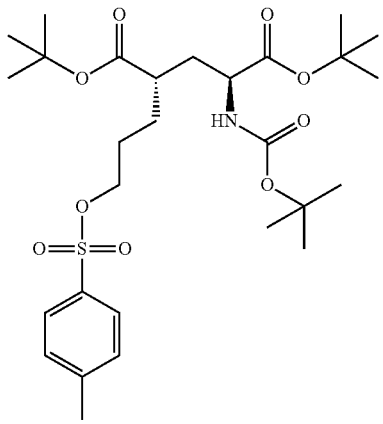 [SMILES: Cc1ccc(S(=O)(=O)OCCC[C@@H](C[C@H](NC(=O)OC(C)(C)C)C(=O)OC(C)(C)C)C(=O)OC(C)(C)C)cc1]

418 mg (1 mmol) of di-tert-butyl (2S,4S)-2-tert-butoxycarbonylamino-4-(3-hydroxypropyl)-pentanedioate 5b were dissolved in 20 mL of dichloromethane and cooled in an ice-bath. After addition of 0.61 g (6 mmol) of triethylamine and 0.38 g (2 mmol) p-toluenesulphonyl chloride, the mixture was stirred on ice for 2 h, overnight at room temperature and then concentrated. The crude product obtained in this manner was chromatographed on silica gel using a hexane/ethyl acetate gradient and the appropriate fractions were combined and concentrated.

Yield: 0.37 g (64.7%)

MS (ESIpos): m/z=572 [m+H]+

1H NMR (300 MHz, CHLOROFORM-0 d ppm 1.37-1.93 (m, 33H) 2.18-2.35 (m, 4H) 4.01-4.16 (m, 3H) 4.84 (d, 1H) 7.35 (d, 2H) 7.78 (d, 2H)

b) di-tert-butyl (2S,4S)-2-tert-Butoxycarbonylamino-4-(3-[F-18]fluoropropyl)-pentanedioate

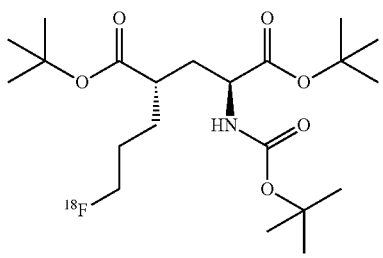 [SMILES: CC(C)(C)OC(=O)N[C@@H](C[C@H](CCC[18F])C(=O)OC(C)(C)C)C(=O)OC(C)(C)C]

[F-18]-Fluoride was prepared by the [O-18](p,n)[F-18] reaction in a cyclotron. The isotope solution (5.2 GBq) was applied to a Sep-Pack Light QMA cartridge. The [F-18]-fluoride was eluted from the cartridge using a Kryptofix 2.2.2/potassium carbonate solution (5 mg K2.2.2, 1 mg potassium carbonate, acetonitrile (1.5 ml), water (0.5 ml). The solvent was removed at 120° C. in a stream of nitrogen with addition of acetonitrile (three times 1 ml).

5 mg (8.7 µmol) di-tert-butyl (2S,4S)-2-tert-Butoxycarbonylamino-4-(3-[toluenesulfonyloxy-propyl)-pentanedioate 6a was added to in 1 mL Acetonitrile and the resulting moisture is 10 min at 110° C. stirred. After cooling to about 60° C., the mixture was passed through a silica-plus cartridge.

The intermediate was purified by HPLC (C18, acetonitrile/water). The HPLC fraction was diluted with water (about 50 ml) and passed through a C18 cartridge. The intermediate was eluted with 1 ml of acetonitrile.

920 MBq (41% d.c.) di-tert-butyl (2S,4S)-2-tert-Butoxycarbonylamino-4-(3-[F-18]fluoropropyl)-pentanedioate 5f were obtained in a synthesis time of 80 min.

i) (2S,4S)-2-Amino-4-(3-[F-18]fluoropropyl)-pentanedioate

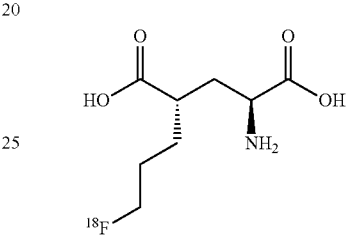

960 MBq of di-tert-butyl(2S,4S)$_2$-tert-Butoxycarbonylamino-4-(3-[F-18]fluoropropyl)-pentanedioate 5f in 1 mL Acetonitrile and then 0.5 mL 4N HCl was added. The mixture was stirred 10 min at the heated temperature of 130° C. (oil bath temperature). After cooling to room temperature, the solution was neutralised with the addition of around 650 pt 2N NaOH.

This gave 870 MBq (95% d.c.) of (2S,4S)-2-amino-4-(3-fluoropropyl)pentanedioate.

Figure 1:
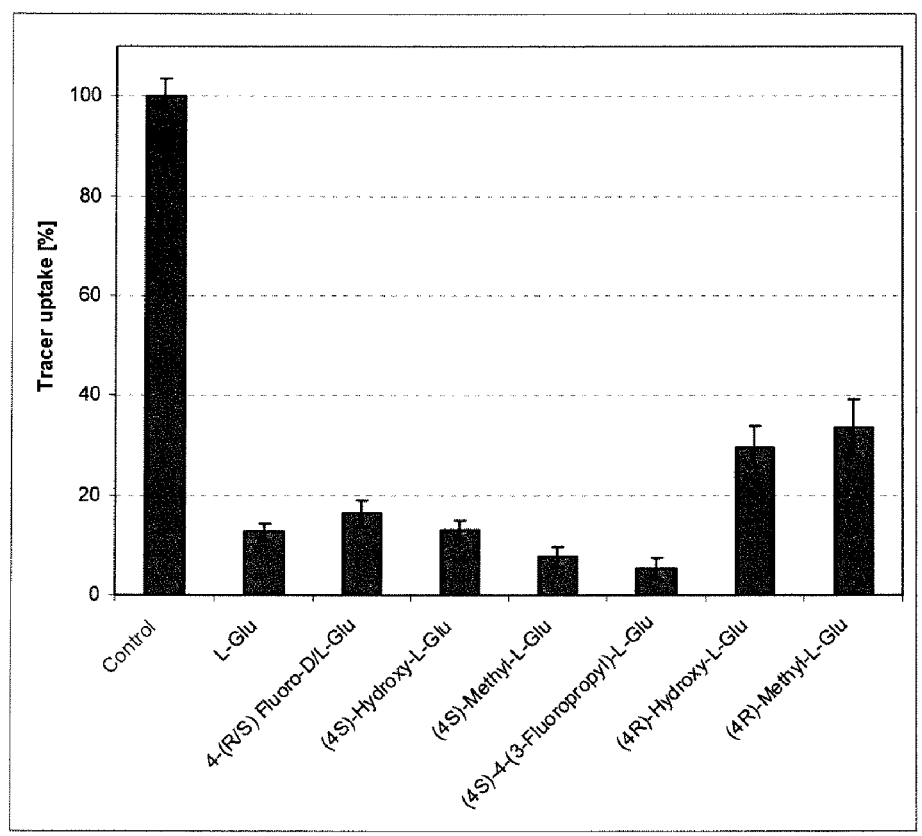
FIGS. 1 and 2 are graphs.
Figure 2:
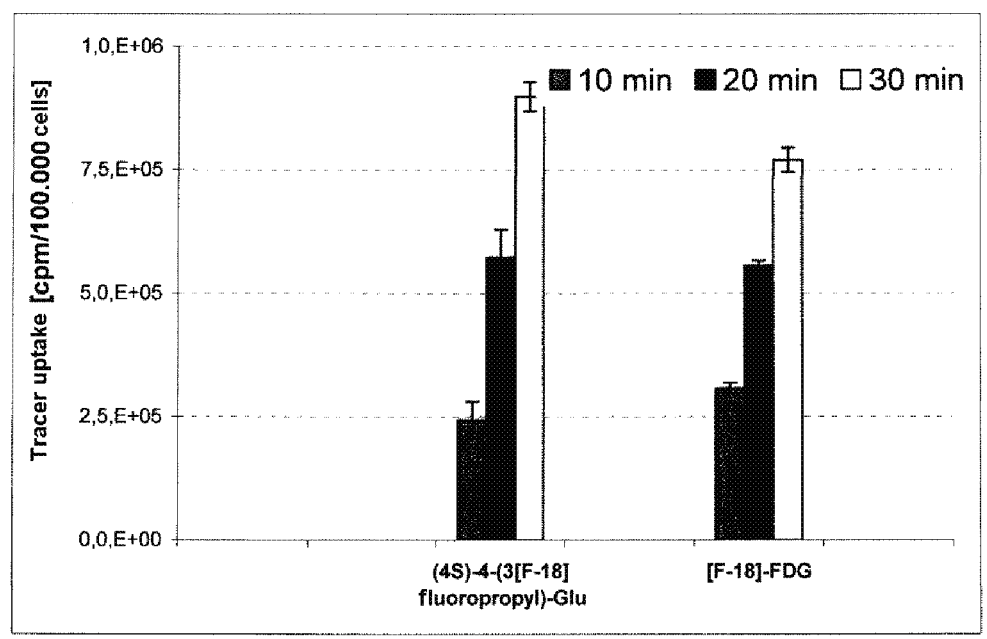
Figure 3:
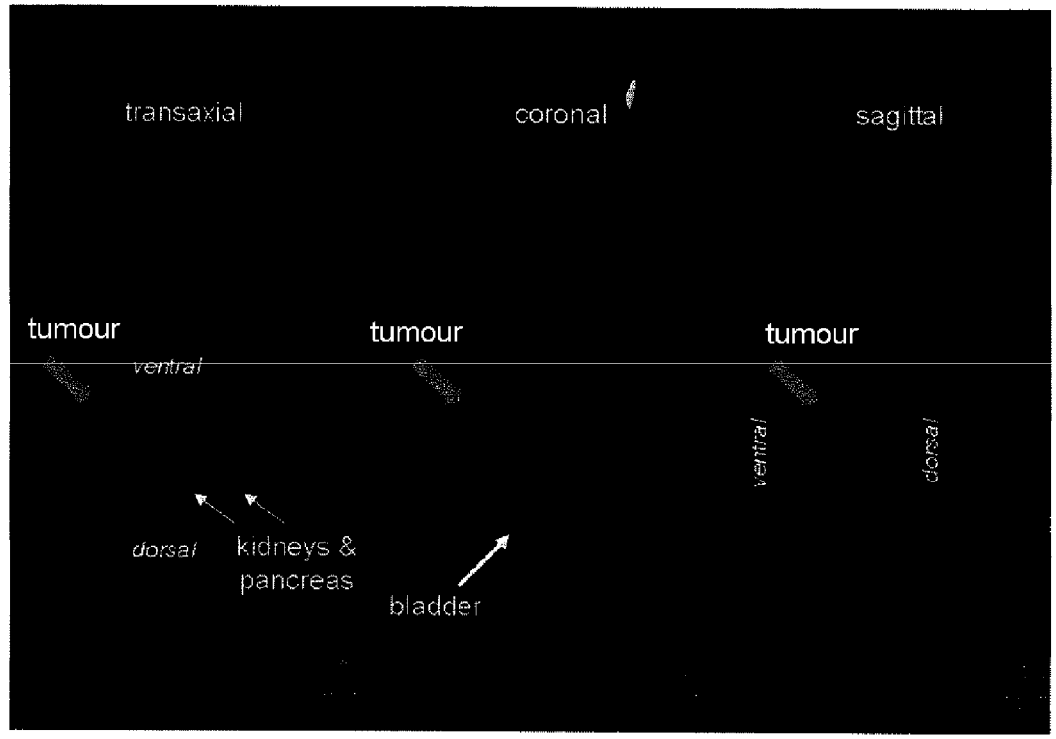
FIGS. 3-5 are images.
Figure 4:
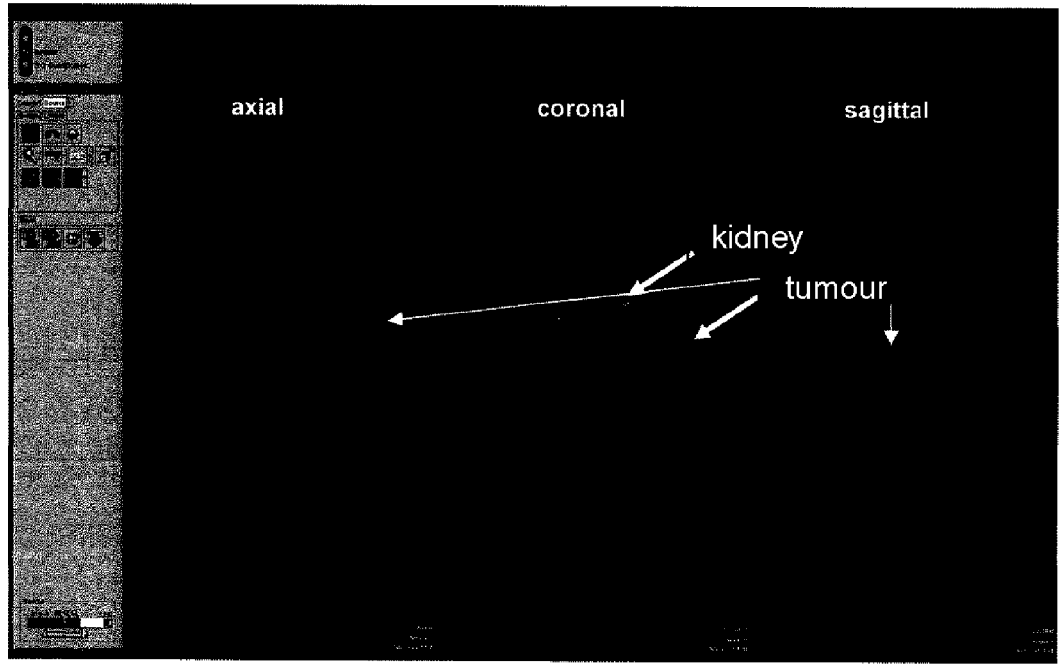
Figure 5:
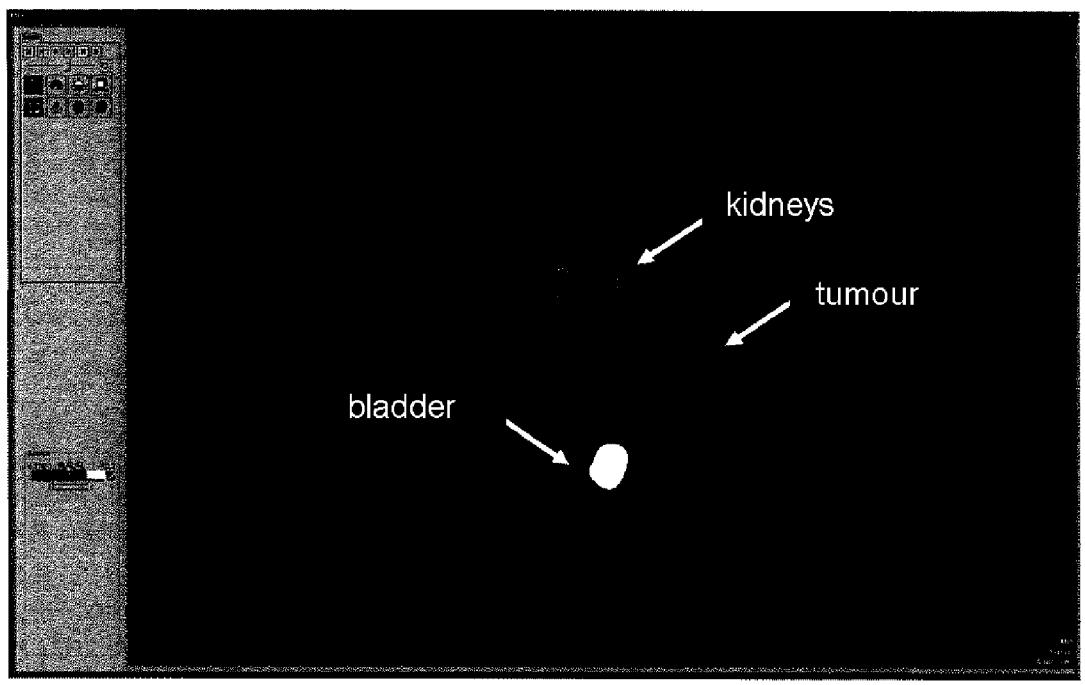
Figure 6:
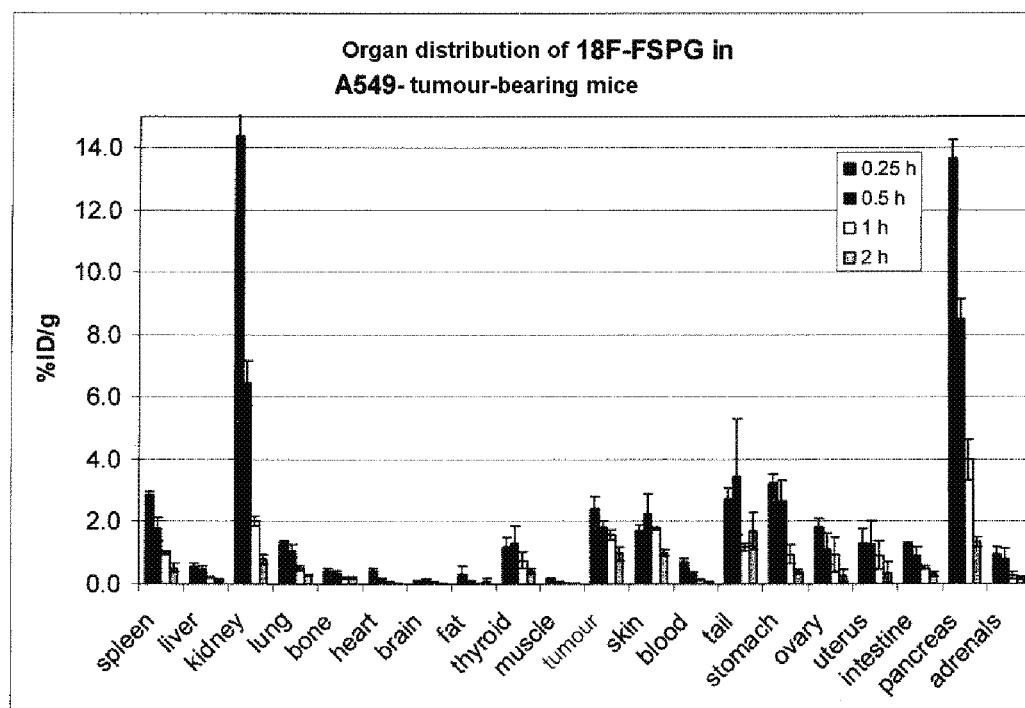
FIG. 6 is a graph.

The invention claimed is:

1. A compound of the formula:

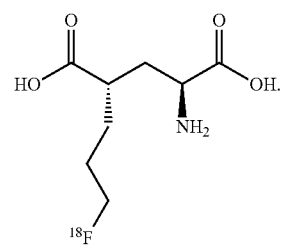

2. A process for preparing the compound according to claim 1, said process comprising:
removing one or more protective groups present in a compound of the formula (II)

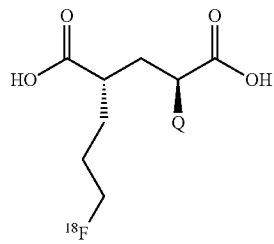 [SMILES: N[C@@H](C[C@H](CCC[18F])C(=O)O)C(=O)O]

(II)

Q represents
a) N(H)-tert-butoxycarbonyl,
b) N(H)-allyloxycarbonyl,
c) N(H)-benzyloxycarbonyl,
d) N(H)-ethoxycarbonyl,
e) N(H)-methoxycarbonyl,
f) N(H)-propoxycarbonyl,
g) N(H)-2,2,2-trichloroethoxycarbonyl,
h) N(H)-1,1-dimethylpropynyl,
i) N(H)-1-methyl-1-phenylethoxycarbonyl,
j) N(H)-1-methyl-1-(4-biphenylyl)ethoxycarbonyl,
k) N(H)-cyclobutylcarbonyl,
l) N(H)-1-methylcyclobutylcarbonyl,
m) N(H)-vinylcarbonyl,
n) N(H)-allylcarbonyl,
o) N(H)-adamantylcarbonyl,
p) N(H)-diphenylmethylcarbonyl,
q) N(H)-cinnamylcarbonyl,
r) N(H)-formyl,
s) N(H)-benzoyl,
t) N(H)-trityl,
u) N(H)-p-methoxydiphenylmethyl,
v) N(H)-di(p-methoxyphenyl)phenylmethyl, w)

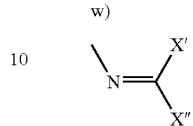

or
x) N-(tert-butoxycarbonyl)$_2$,
in which
X' and X" independently of one another represent
a) branched or straight-chain $C_1$-$C_5$ alkyl,
b) substituted or unsubstituted aryl,
c) substituted or unsubstituted aralkyl or
d) substituted or unsubstituted heteroaryl.

3. A method of imaging a patient for tumor disorders comprising imaging a patient who has been administered a compound according to claim 1.

4. An imaging kit, comprising a compound according to claim 1.

5. A pharmaceutical composition, comprising a compound according to claim 1 and a suitable pharmaceutical carrier substance.

6. A compound according to claim 1, suitable for imaging in a dosage range of 37-600 MBq.

7. The compound according to claim 6, suitable for imaging in a dosage range of 150 MBq-370 MBq.

* * * * *